(12) United States Patent
Thaler et al.

(10) Patent No.: US 10,501,417 B2
(45) Date of Patent: Dec. 10, 2019

(54) SYNTHESIS OF INDAZOLES

(71) Applicant: Bayer Pharma Aktiengesellschaft, Berlin (DE)

(72) Inventors: Tobias Thaler, Köln (DE); Johannes Platzek, Berlin (DE); Nicolas Guimond, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/097,065

(22) PCT Filed: Apr. 25, 2017

(86) PCT No.: PCT/EP2017/059744
§ 371 (c)(1),
(2) Date: Oct. 26, 2018

(87) PCT Pub. No.: WO2017/186689
PCT Pub. Date: Nov. 2, 2017

(65) Prior Publication Data
US 2019/0106407 A1    Apr. 11, 2019

(30) Foreign Application Priority Data

Apr. 29, 2016  (EP) .................................... 16167652

(51) Int. Cl.
| C07D 401/12 | (2006.01) |
| C07D 213/81 | (2006.01) |
| C07D 213/54 | (2006.01) |
| C07D 231/56 | (2006.01) |

(52) U.S. Cl.
CPC ......... *C07D 213/81* (2013.01); *C07D 213/54* (2013.01); *C07D 231/56* (2013.01); *C07D 401/12* (2013.01); *C07B 2200/13* (2013.01)

(58) Field of Classification Search
CPC ... C07D 401/12; C07D 213/55; C07D 231/56
USPC ............................. 546/275.7, 326; 548/362.1
See application file for complete search history.

(56) References Cited

U.S. PATENT DOCUMENTS

| 8,293,923 | B2 | 10/2012 | Guckian et al. |
| 9,951,086 | B2 | 4/2018 | Bothe |
| 10,308,634 | B2 | 6/2019 | Bothe |
| 2005/0054627 | A1 | 3/2005 | Carter et al. |
| 2013/0274241 | A1 | 10/2013 | Jorand-Lebrun et al. |
| 2015/0133422 | A1 | 5/2015 | Crosignani et al. |
| 2016/0311833 | A1 | 10/2016 | Gummadi |
| 2018/0201609 | A1 | 7/2018 | Bothe |
| 2019/0071432 | A1 | 3/2019 | Bothe |
| 2019/0112270 | A1 | 4/2019 | Thaler |
| 2019/0125736 | A1 | 5/2019 | Rausch |
| 2019/0144420 | A1 | 5/2019 | Thaler |

FOREIGN PATENT DOCUMENTS

| EP | 2045253 A1 | 4/2009 | |
| WO | WO2007/091107 A1 | 8/2007 | |
| WO | WO2011/043479 A1 | 4/2011 | |
| WO | WO2011/153588 A1 | 12/2011 | |
| WO | WO2013/106254 A1 | 7/2013 | |
| WO | WO2015/091426 A1 | 6/2015 | |
| WO | WO2015091426 A1 | 6/2015 | |
| WO | WO2016/083433 A1 | 6/2016 | |
| WO | WO 2016/174183 A1 * | 11/2016 | ........... C07D 401/12 |
| WO | WO2016174183 A1 | 11/2016 | |
| WO | WO2017148902 A1 | 9/2017 | |
| WO | WO2017186693 A1 | 11/2017 | |
| WO | WO2017186700 A1 | 11/2017 | |
| WO | WO2017186703 A1 | 11/2017 | |
| WO | WO2017207386 A1 | 12/2017 | |
| WO | WO2017207481 A8 | 11/2018 | |

OTHER PUBLICATIONS

Schlosser, M. et al.: The direct metalation and subsequent functionalization of trifluoromethyl-substituted pyridines and quinolines. European J. Org. Chem., vol. 8, pp. 1569-1575, 2003.*
Janeway, C.A. et al. (2002). "Innate Immune Recognition," *Annu. Rev. Immunol.* 20:197-216.
Dinarello, C.A. (2009). "Immunological and Inflammatory Functions of the Interleukin-1 Family," *Annu. Rev. Immunol.* 27:519-550.
Flannery, S. et al. (2010). "The interleukin-1 receptor-associated kinases: Critical regulators of innate immune signaling," *Biochemical Pharmacology* 80:1981-1991.
Suzuki, N. et al. (2002). "Severe impairment of interleukin-1 and Toll-like receptor signaling in mice lacking IRAK-4," *Nature* 416:750-754.
Davidson, D.J. et al. (2006). "IRAK-4 Mutation (Q293X): Rapid Detection and Characterization of Defective Post-Transcriptional TLR/IL-1R Responses in Human Myeloid and Non-Myeloid Cells," *J. Immunol* 177:8202-8211.

(Continued)

*Primary Examiner* — Charanjit Aulakh
(74) *Attorney, Agent, or Firm* — Morrison & Foerster LLP

(57) ABSTRACT

The present invention relates to a novel method of preparing a 2-substituted indazole of structure: (I), to intermediate compounds, and to the use of intermediate compounds for the preparation of said 2-substituted indazole.

(I)

22 Claims, 1 Drawing Sheet

(56) References Cited

OTHER PUBLICATIONS

Ku, C. et al. (2007). "Selective predisposition to bacterial infections in IRAK-4-deficient children: IRAK-4-dependent TLRs are otherwise redundant in protective immunity," *JEM* 204(10):2407-2422.

Kim, T.W. et al. (2007). "A critical role for IRAK4 kinase activity in Toll-like receptor-mediated innate immunity," *JEM* 204(5):1025-1036.

Kollewe, C. et al. (2004). "Sequential Autophosphorylation Steps in the Interleukin-1 Receptor-associated Kinase-1 Regulate its Availability as an Adapter in Interleukin-1 Signaling," *The Journal of Biological Chemistry* 279(7):5227-5236.

Motshwene, P.G. et al. (2009). "An Oligomeric Signaling Platform Formed by the Toll-like Receptor Signal Transducers MyD88 and IRAK-4," *The Journal of Biological Chemistry* 284(37):25404-25411.

Wang, C. et al. (2001). "TAK1 is a ubiquitin-dependent kinase of MMK and IKK," *Nature* 412: 346-351.

Holtmann, H. et al. (2001). "The MAPK Kinase Kinase TAK1 Plays a Central Role in Coupling the Interleukin-1 Receptor to Both Transcriptional and RNA-targeted Mechanisms of Gene Regulation," *The Journal of Biological Chemistry* 276(5): 3508-3516.

Datta, S. et al. (2004). "Toll IL-1 Receptors Differ in Their Ability to Promote the Stabilization of Adenosine and Uridine-Rich Elements Containing mRNA," *J Immunol* 173: 2755-2761.

Wan, Y.Y. et al. (2006). "The kinase TAK1 integrates antigen and cytokine receptor signaling for T cell development, survival and function," *Nature Immunology* 7(8): 851-858.

McGettrick, A.F. et al. (2007). "Toll-like receptors: key activators of leucocytes and regulator of haematopoiesis," *British Journal of Haematology* 139: 185-193.

Rekhter, M. et al. (2008). "Genetic ablation of IRAK4 kinase activity inhibits vascular lesion formation," *Biochemical and Biophysical Research Communications* 367: 642-648.

Maekawa, Y. et al. (2009). "Survival and Cardiac Remodeling After Myocardial Infarction are Critically Dependent on the Host Innate Immune Interleukin-1 Receptor-Associated Kinase-4 Signaling: A Regulator of Bone Marrow-Derived Dendritic Cells," *Circulation* 120: 1401-1414.

Staschke, K.A. et al. (2009). "IRAK4 kinase Activity is Required for Th17 Differentiation and Th17-mediated Disease," *J Immunol* 183(1): 568-577.

Kim, T.W. et al. (2011). "The critical role of IRAK4-mediated NFkB activation in modified LDL-induced atherosclerosis," *J Immunol* 186(5): 2871-2880.

Cameron, B. et al. (2012). "Loss of Interleukin Receptor Associated Kinase 4 Signaling Suppresses Amyloid Pathology and Alters Microglial Phenotype in a Mouse Model of Alzheimer's Disease," *J. Neurosci* 32(43): 15112-15123.

Valaperti, A. et al. (2013). "Innate Immune Interleukin-1 Receptor-Associated Kinase 4 Exacerbates Viral Myocarditis by Reducing CCR5$^+$CD11b$^+$Monocyte Migration and Impairing Interferon Production," *Circulation* 128: 1542-1554.

Sun, M. et al. (2014). "The Role of Interleukin-1 Receptor-Associated Kinases in Vogt-Koyanagi-Herada Disease," *PLOS ONE* 9(4): 1-8.

Zambrano-Zaragoza, J.F. et al. (2014). "Th17 Cells in Autoimmune and Infectious Diseases," *International Journal of Inflammation* 1-12.

Scanzello, C.R. et al. (2008). "Innate immune system activation in osteoarthritis: is osteoarthritis a chronic wound?" *Current Opinion in Rheumatology* 20: 565-572.

Roger, T. et al. (2009). "Protection from lethal Gram-negative bacterial sepsis by targeting Toll-like receptor 4," *PNAS* 106(7): 2348-2352.

Gambuzza, M. et al. (2011). "Targeting Toll-like receptors: Emerging therapeutics from multiple sclerosis management," *Journal of Neuroimmunology* 239: 1-12.

Fresno, M. et al. (2011). "Toll-like receptors, inflammation, metabolism and obesity," *Archives of Physiology and Biochemistry* 117(3): 151-164.

Volin, M.V. et al. (2011). "Interleukin-18: A Mediator of Inflammation and Angiogenesis in Rheumatoid Arthritis," *Journal of Interferon & Cytokine Research* 31(10): 745-781.

Akash, M.S.H. et al. (2012). "Interleukin-1 Receptor Antagonist: A New Therapy for Type 2 Diabetes Mellitus," *Journal of Pharmaceutical Sciences* 101(5): 1647-1658.

Goh, F.G. et al. (2012). "Intrinsic danger: activation of Toll-like receptors in rheumatoid arthritis," *Rheumatology* 51: 7-23.

Dasu, M.R. et al. (2012). "Toll-like receptors and diabetes: a therapeutic perspective," *Clinical Science* 122: 203-214.

Ramirez, S.R. et al. (2012). "Toll-like Receptors and Diabetes Complications: Recent Advances," *Current Diabetes Reviews* 8: 480-488.

Li, J. et al. (2013). "Toll-like receptors as therapeutic targets for autoimmune connective tissue diseases," *Pharmacology & Therapeutics* 138: 441-451.

Sedimbi, S.K. et al. (2013). "IL-18 in inflammatory and autoimmune disease," *Cell. Mol. Life Sci.* 70: 4795-4802.

Talabot-Ayer, D. et al. (2014). "Immune-mediated experimental arthritis in IL-33 deficient mice," *Cytokine* 69: 68-74.

Gilliet, M. et al. (2004). "Psoriasis Triggered by Toll-like Receptor 7 Agonist Imiquimod in the Presence of Dermal Plasmacytoid Dendritic Cell Precursors," *Arch Dermatol* 140: 1490-1495.

Niebuhr, M. et al. (2008). "Dysrregulation of toll-like receptor-2 (TLR-2)-induced effects in monocytes from patients with atopic dermatitis: impact of the TLR-2 R753Q polymorphism," *Allergy* 63: 728-734.

Miller, L.S. (2008). "Toll-like receptors in skin," *Adv Dermatol.* 24: 71-87.

Terhorst, D. et al. (2010). "The Role of Toll-Like Receptors in Host Defenses and Their Relevance to Dermatologic Disease," *Am J. Clin Dermatol* 11(1): 1-10.

Viguier, M. et al. (2010). "Successful Treatment of Generalized Pustular Psoriasis With the Interleukin-1-Receptor Antagonist Anakainra: Lack of Correlation with IL1RN Mutations," *Annals of Internal Medicine* 153: 66-67.

Cevikbas, F. et al. (2012). "IL-33: A Novel Danger Signal System in Atopic Dermatitis," *Journal of Investigative Dermatology* 132: 1326-1329.

Minkis, K. et al. (2012). "Interleukin 1 Receptor Antagonist Deficiency Presenting as Infantile Pustulosis Mimicking Infantile Pustular Psoriasis," *Arch Dermatol.* 148(6): 747-752.

Dispenza, M.C. et al. (2012). "Systemic isotretinoin therapy normalizes exaggerated TLF-2-mediated innate immune responses in acne patients," *J. Invest Dermatol.* 132(9): 2198-2205.

Gresnigt, M.S. et al. (2013). "Biology of IL-36 cytokines and their role in disease," *Seminars in Immunology* 25: 458-465.

Selway, J.L. et al. (2013). "Toll-like receptor 2 activation and comedogenesis: implications for the pathogenesis of acne," *BMC Dermatology* 13(10): 1-7.

Wollina, U. et al. (2013). "Acne inversa (Hidradenitis suppurativa): A review with a focus on pathogenesis and treatment," *Indian Dermatology Online Journal* 4(1): 1-11.

Foster, A.M. et al. (2014). "IL-36 promotes myeloid cell infiltration, activation and inflammatory activity in skin," *J Immunol.* 192(12): 6053-6061.

Ramirez Cruz, N.E.R. et al. (2004). "Toll-like receptors: dysregulation in vivo in patients with acute respiratory distress syndrome," *Revista Alergia Mexico* 51(6): 210-217.

Jeyaseelan, S. et al. (2005). "Distinct Roles of Pattern Recognition Receptors CD14 and Toll-Like Receptor 4 in Acute Lung Injury," *Infection and Immunity* 73(3): 1754-1763.

Seki, H. et al. (2010). "Effect of Toll-like receptor 4 inhibitor on LPS-induced lung injury," *Inflamm. Res.* 59: 837-845.

Xiang, M. et al. (2010). "Association of Toll-Like Receptor Signaling and Reactive Oxygen Species: A Potential Therapeutic Target for Posttrauma Acute Lung Injury," *Mediators of Inflammation* 8 pages.

(56) References Cited

OTHER PUBLICATIONS

Margaritopoulous, G.A. et al. (2010). "Investigation of Toll-like receptors in the pathogenesis of fibrotic and granulomatous disorders: a bronchoalveolar lavage study," *Fibrogenesis & Tissue Repair* 3(20): 1-9.
Hilberath, J.N. et al. (2017). "Resolution of Toll-like receptor 4-mediated acute lung injury is linked to eicosanoids and suppressor of cytokine signaling 3," *The FASEB Journal* 25(6): 1827-1835.
Nadigel, J. et al. (2011). "Cigarette smoke increases TLR4 and TLR9 expression and induces cytokine production from CD8+ T cells in chronic obstructive pulmonary disease," *Respiratory Research* 12(149): 1-13.
Kovach, M.A. et al. (2011). "Toll like receptors in diseases of the lung," *International Immunopharmacology* 11: 1399-1406.
Bauer, E.M. et al. (2012). "High Mobility Group Box 1 Contributes to the Pathogenesis of Experimental Pulmonary Hypertension via Activation of Toll-like Receptor 4," *Molecular Medicine* 18: 1509-1518.
Han, Y. et al. (2013). "Associations of pri-miR-34b/c and pre-miR-196a2 Polymorphisms and Their Multiplicative Interactions with Hepatitis B Virus Mutations with Hepatocellular Carcinoma Risk," *PLOS One* 8(3): 1-9.
Freeman, C.M. et al. (2013). "Lung CD8+ T cells in COPD have increased expression of bacterial TLRs," *Respiratory Research* 14(13): 1-13.
Dubaniewicz, A. (2013). "Microbial and human heat shock proteins as 'danger signals' in sarcoidosis," *Human Immunology* 74: 1550-1558.
Liu-Bryan, R. et al. (2005). "Innate Immunity Conferred by Toll-like Receptors 2 and 4 and Myeloid Differentiation Factor 88 Expression is Pivotal to Monosodium Urate Monohydrate Crystal-Inducted Inflammation," *Arthritis & Rheumatism* 52(9): 2936-2946.
Christensen, S.R. et al. (2006). "Toll-like Receptor 7 and TLR9 Dictate Autoantibody Specificity and Have Opposing Inflammatory and Regulatory Roles in a Murine Model of Lupus," *Immunity* 25: 417-428.
Cario, E. (2010). "Toll-like Receptors in Inflammatory Bowel Diseases: A Decade Later," *Inflamm Bowel Dis* 16(9): 1583-1597.
Nickerson, K.M. et al. (2010). "TLR9 Regulates TLR7- and MyD88-Dependent Autoantibody Production and Disease in a Murine Model of Lupus," *J Immunol* 184: 1840-1848.
Rakoff-Nahoum, S. et al. (2006). "Role of Toll-like Receptors in Spontaneous Commensal-Dependent Colitis," *Immunity* 25: 319-329.
Heimesaat, M.M. et al. (2007). "Shift Towards Pro-inflammatory Intestinal Bacteria Aggravates Acute Murine Colitis via Toll-like Receptors 2 and 4," *PLoS ONE* 7: 1-7.
Kobori, A. et al. (2010). "Interleukin-33 expression is specifically enhanced in inflamed mucosa of ulcerative colitis," *J. Gastroenterol* 45: 999-1007.
Shi, Y. et al. (2010). "Monosodium urate crystals in inflammation and immunity," *Immunological Reviews* 233: 203-217.
Leventhal, J.S. et al. (2012). "Toll-like receptors in transplantation: sensing and reacting to injury," *Kidney International* 81: 826-832.
Chen, D-Y. et al. (2013). "Involvement of TLR7 MyD88-dependent signaling pathway in the pathogenesis of adult-onset Still's disease," *Arthritis Research & Therapy* 15: 1-12.
Hao, L-Y. et al. (2013). "Inflammasomes in inflammatory bowel disease pathogenesis," *Current Opinion* 29(4): 363-369.
Kreisel, D. et al. (2013). "Innate immunity and organ transplantation: focus on lung transplantation," *Transpl Int.* 26(1): 2-10.
Walsh, D. et al. (2013). "Pattern recognition receptors-Molecular orchestrators of inflammation in inflammatory bowel disease," *Cytokine & Growth Factor Reviews* 24: 91-104.
Zhu, F-G. et al. (2013). "A novel antagonist of Toll-like receptors 7, 8 and 9 suppresses lupus disease-associated parameters in NZBW/F1 mice," *Autoimmunity* 46(7): 419-428.
Yap, D. Y. H. et al. (2013). "The role of cytokines in the pathogenesis on systemic lupus erythematosus—from bench to bedside," *Nephrology* 18: 243-255.
Akoum, A. et al. (2007). "Imbalance in the expression of the activating type I and the inhibitory type II interleukin 1 receptors in endometriosis," *Human Reproduction* 22(5): 1464-1473.
Allhorn, S. et al. (2008). "TLR3 and TLR4 expression in healthy and diseased human endometrium," *Reproductive Biology and Endocrinology* 6(40): 1-11.
Lawson, C. et al. (2008). Abnormal interleukin 1 receptor types I and II gene expression in eutopic and ectopic endometrial tissues of women with endometriosis, *Journal of Reproductive Immunology* 77: 75-84.
Seneviratne, A.N. et al. (2012). "Toll-like receptors and macrophage activation in atherosclerosis," *Clinica Chimica Acta* 413: 3-14.
Sikora, J. et al. (2012). "Imbalance in Cytokines from Interleukin-1 Family—Role in Pathogenesis of Endometriosis," *American Journal of Reproductive Immunology* 68: 138-145.
Falck-Hansen, M. et al. (2013). "Toll-Like Receptors in Atherosclerosis," *Int. J. Mol. Sci.* 14: 14008-14023.
Khan, K. N. et al. (2013). "Toll-like receptor system and endometriosis," *J. Obstet. Gynaecol. Res.* 39(8): 1281-1292.
Santulli, P. et al. (2013). "Profibrotic interleukin-33 is correlated with uterine leiomyoma tumour burden," *Human Reproduction* 28(8): 2126-2133.
Kaarniranta, K. et al. (2009). "Age-related macular degeneration: activation of innate immunity system via pattern recognition receptors," *J Mol Med* 87: 117-123.
Sun, Y. et al. (2009). "Inhibition of Corneal Inflammation by the TLR4 Antagonist Eritoran Tetrasodium (E5564)," *Invest Ophthalmol Vis Sci.* 50(3): 1247-1254.
Redfern, R.L. et al. (2010). "Toll-like receptors in ocular surface disease," *Experimental Eye Research* 90: 679-687.
Kezic, J. et al. (2011). "Endotoxin-induced uveitis is primarily dependent on radiation-resistant cells and on MyD88 but not TRIF," *Journal of Leukocyte Biology* 90(2): 305-311.
Chang, J.H. et al. (2012). "Recent advances in Toll-like receptors and anterior uveitis," *Clinical and Experimental Ophthalmology* 40: 821-828.
Guo, H. et al. (2012). "Toll-like receptor 2 siRNA suppresses corneal inflammation and attenuates *Aspergillus fumigatus* keratitis in rats," *Immunology and Cell Biology* 90: 352-357.
Lee, H.S. et al. (2012). "Expression of Toll-like Receptor 4 Contributes to Corneal Inflammation in Experimental Dry Eye Disease," *Invest Ophthalmol Vis Sci.* 53(9): 5632-5640.
Qi, Y. et al. (2014). "Retinal Ischemia/Reperfusion Injury is Mediated by Toll-like Receptor 4 Activation of NLRP3 Inflammasomes," *IOVS* 55(9): 5466-5475.
Oyama, J-I. et al. (2004). "Reduced Myocardial Ischemia-Reperfusion Injury in Toll-Like Receptor 4-Deficient Mice," *Circulation* 109: 784-789.
Timmers, L. et al. (2008). "Toll-Like Receptor 4 Mediates Maladaptive Left Ventricular Remodeling and Impairs Cardiac Function After Myocardial Infarction," *Circulation Research* 102: 257-264.
Fang, Y. et al. (2011). "Toll-like receptor and its roles in myocardial ischemic/reperfusion injury," *Med Sci Monit* 17(4): RA100-109.
Bijani, F.M. et al. (2012). "Toll-like Receptor Signaling Pathways in Cardiovascular Diseases: Challenges and Opportunities," *International Reviews of Immunology* 31: 379-395.
Bomfim, G.F. et al. (2012). "Toll like receptor 4 contributes to blood pressure regulation and vascular contraction in spontaneously hypertensive rat," *Clin Sci (Lond)* 122(11): 535-543.
Christia, P. et al. (2013). "Targeting inflammatory pathways in myocardial infarction," *Eur J. Clin Invest.* 43(9): 986-995.
Thompson, J.A. et al. (2013). "Potential role of Toll-like receptors in programming of vascular dysfunction," *Clinical Science* 125: 19-25.
Brough, D. et al. (2011). "Regulation of interleukin-1 in acute brain injury," *Trends in Pharmacological Sciences* 32(10): 617-622.
Carty, M. et al. (2011). "Evaluating the role of Toll-like receptors in diseases of the central nervous system," *Biochemical Pharmacology* 81: 825-837.
Kitazawa, M. et al. (2011). "Blocking IL-1 Signaling Rescues Cognition, Attenuates Tau Pathology, and Restores Neuronal β-Catenin Pathway Function in an Alzheimer's Disease Model," *The Journal of Immunology* 187: 6539-6549.

(56) References Cited

OTHER PUBLICATIONS

Lim, J-E. et al. (2011). "MyD88 Deficiency Ameliorates β-Amyloidosis in an Animal Model of Alzheimer's Disease," *The American Journal of Pathology* 179(3): 1095-1103.
Béraud, D. et al. (2012). "Misfolded α-synuclein and toll-like receptors: therapeutic targets for Parkinson's disease," *Parkinsonism and Related Disorders* 18S1: S17-S20.
Denes, A. et al. (2013). "Central and haematopoietic interleukin-1 both contribute to ischaemic brain injury in mice," *Disease Models & Mechanisms* 6: 1043-1048.
Noelker, C. et al. (2013). "Toll like receptor 4 mediates cell death in a mouse MPTP model of Parkinson disease," *Scientific Reports* 3(1393): 1-5.
Wang, Y-C. et al. (2013). "Toll-Like Receptor 4 Antagonist Attenuates Intracerebral Hemorrhage-Induced Brain Injury," *Stroke* 44: 2545-2552.
Wolf, G. et al. (2008). "Interleukin-1 signaling in required for induction and maintenance of postoperative incisional pain: Genetic and pharmacological studies in mice," *Brain, Behavior, and Immunity* 22: 1072-1077.
Kim, D. et al. (2009). "Toll-Like Receptors in Peripheral Nerve Injury and Neuropathic Pain," *Current Topics in Microbiology and Immunology* 336: 169-186.
Del Rey, A. et al. (2012). "Chronic neuropathic pain-like behavior and brain-borne IL-1β," *Ann. N.Y. Acad. Sci.* 1262: 101-107.
Guerrero, A.T.G. et al. (2012). "Toll-like receptor 2/MyD88 signaling mediates zymosan-induced joint hypernociception in mice: Participation of TNF-α, IL-1β and CXCL1/KC," *European Journal of Pharmacology* 674: 51-57.
Kwok, Y.H. et al. (2012). "Increased Responsiveness of Peripheral Blood Mononuclear Cells to In Vitro TLF 2, 4 and 7 Ligand Stimulation in Chronic Pain Patients," *PLOS One* 7(8): 1-8.
Nicotra, L. et al. (2012). "Toll-Like Receptors in Chronic Pain," *Exp Neurol.* 234(2): 316-329.
Chopra, P. et al. (2013). "Treatment of Complex Regional Pain Syndrome (CRPS) Using Low Dose Naltrexone (LDN)," *J Neuroimmune Pharmacol* 8: 470-476.
David, B.T. et al. (2013). "A toll-like receptor 9 antagonist reduces pain hypersensitivity and the inflammatory response in spinal cord injury," *Neurobiology of Disease* 54: 194-205.
Han, P. et al. (2013). "Interleukin-33 Mediates Formalin-Induced Inflammatory Pain in Mice," *Neuroscience* 241: 59-66.
Liu, T. et al. (2013). "New insights into the mechanisms of itch: are pain and itch controlled by distinct mechanisms?" *Pflugers Arch.* 465(12): 1-24.
Stokes, J.A. (2013). "Toll-like receptor signaling adapter proteins govern spread of neuropathic pain and recovery following nerve injury in male mice," *Journal of Neuroinflammation* 10(148): 1-14.
Zhao, J. et al. (2013). "Spinal Interleukin-33 and its Receptor ST2 Contribute to Bone Cancer-Induced Pain in Mice," *Neuroscience* 253: 172-182.
Liu, X-J. et al. (2014). "Nociceptive neurons regulate innate and adaptive immunity and neuropathic pain through MyD88 adapter," *Cell Research* 24: 1374-1377.
Ngo, V.N. et al. (2011). "Oncogenically active MYD88 mutations in human lymphoma," *Nature* 470: 115-121.
Puente, X.S. et al. (2011). "Whole-genome sequencing identifies recurrent mutations in chronic lymphocytic leukaemia," *Nature* 475: 101-105.
Srivastava, R. et al. (2012). "Augmentation of Therapeutic Responses in Melanoma by Inhibition of IRAK-1,-4," *Cancer Research* 72(23): 6209-6216.
Treon, S.P. et al. (2012). "MYD88 L265P Somatic Mutation in Waldenström's Macroglobulinemia," *The New England Journal of Medicine* 367(9): 826-833.
Choi, J-W. et al. (2013). "MYD88 expression and L265P mutation in diffuse large B-cell lymphoma," *Human Pathology* 44: 1375-1381.
Liang, B. et al. (2013). "Myeloid Differentiation Factor 88 Promotes Growth and Metastasis of Human Hepatocellular Carcinoma," *Clinical Cancer Research* 19(11): 2905-2916.
Kfoury, A. et al. (2013). "MyD88 in DNA Repair and Cancer Cell Resistance to Genotoxic Drugs," *JNCI* 105(13): 937-946.
Narayanan, S. et al. (2008). "Interleukin-1 Receptor-1-deficient Mice Show Attenuated Production of Ocular Surface Inflammatory Cytokines in Experimental Dry Eye," *Cornea* 27(7): 811-817.
Henderson, C. et al. (2010). "Monogenic IL-1 Mediated Autoinflammatory and Immunodeficiency Syndromes: Finding the Right Balance in Response to Danger Signals," *Clin Immunol.* 135(2): 210-222.
Dinarello, C.A. (2011). "A clinical perspective of IL-1 β as the gatekeeper of inflammation," *Eur. J. Immunol.* 41: 1203-1217.
Gül, A. et al. (2012). "Interleukin-1 β-regulating antibody XOMA 052 (gevokizumab) in the treatment of acute exacerbations of resistant uveitis of Behçet's disease: an open-label pilot study," *Ann Rheum Dis* 71:563-566.
Pettersson, T. et al. (2012). "Setting up TRAPS," *Annals of Medicine* 44: 109-118.
Ruperto, N. et al. (2012). "Two Randomized Trials of Canakinumab in Systemic Juvenile Idiopathic Arthritis," *The New England Journal of Medicine* 367(25): 2396-2406.
Nordström, D. et al. (2012). "Beneficial Effect of Interleukin 1 Inhibition with Anakinra in Adult-onset Still's Disease. An Open, Randomized, Multicenter Study," *The Journal of Rheumatology* 39(10): 2008-2011.
Vijmasi, T. et al. (2013). "Topical administration of interleukin-1 receptor antagonist as a therapy for aqueous-deficient dry eye in autoimmune disease," *Molecular Vision* 19: 1957-1965.
Yamada, A. et al. (2013). "Targeting IL-1 in Sjögren's syndrome," *Expert Opin. Ther. Targets* 17(4): 393-401.
Akcay, A. et al. (2011). "IL-33 Exacerbates Acute Kidney Injury," *J Am Soc Nephrol* 22: 2057-2067.
Kang, M-J. et al. (2007). "IL-18 is Inducted and IL-18 Receptor α Plays a Critical Role in the Pathogenesis of Cigarette Smoke-Induced Pulmonary Emphysema and Inflammation," *J Immunol* 178: 1948-1959.
Imaoka, H. et al. (2008). "Interleukin-18 production and pulmonary function in COPD," *Eur Respir J.* 31: 287-297.
Couillin, I. et al. (2009). "IL-1R1/MyD88 Signaling in Critical for Elastase-Induced Lung Inflammation and Emphysema," *J Immunol* 183: 8195-8202.
Abbate, A. et al. (2010). "Interleukin-1 Blockade with Anakinra to Prevent Adverse Cardiac Remodeling After Acute Myocardial Infarction (Virginia Commonwealth University Anakinra Remodeling Trial [VCU-ART] Pilot Study)," *Am J Cardiol* 105: 1371-1377.
Lloyd, C.M. et al. (2010). "IL-33 family members and asthma—bridging innate and adaptive immune responses," *Curr Opin Immunol* 22(6): 800-806.
Pauwels, N.S. et al. (2011). "Role of IL-1 α and the NIrp3/caspase-1/IL-1 β axis in cigarette smoke-induced pulmonary inflammation and COPD," *Eur Respir J* 38: 1019-1028.
Haenuki, Y. et al. (2012). "A critical role of IL-33 in experimental allergic rhinitis," *J Allergy Clin Immunol* 130(1): 184-194.
Yin, H. et al. (2012). "Adenovirus-mediated delivery of soluble ST2 attenuates ovalbumin-induced allergic asthma in mice," *Clinical & Experimental Immunology* 170: 1-9.
Abbate, A. et al. (2013). "Effects of Interleukin-1 Blockade With Anakinra on Adverse Cardiac Remodeling and Heart Failure After Acute Myocardial Infarction [from the Virginia Commonwealth University-Anakinra Remodeling Trial (2) (VCU-ART2) Pilot Study]," *The American Journal of Cardiology* 111: 1394-1400.
Byers, D.E. et al. (2013). "Long-term IL-33-producing epithelial progenitor cells in chronic obstructive lung disease," *The Journal of Clinical Investigation* 123(9): 3967-3982.
Bunting, M.M. et al. (2013). "Interleukin-33 Drives Activation of Alveolar Macrophages and Airway Inflammation in a Mouse Model of Acute Exacerbation of Chronic Asthma," *BioMed Research International* 10 pages.
Kawayama, T. et al. (2012). "Interleukin-18 in Pulmonary Inflammatory Diseases," *Journal of Interferon & Cytokine Research* 32(10): 443-451.

(56) References Cited

OTHER PUBLICATIONS

Martínez-González, I. et al. (2013). "Human Mesenchymal Stem Cells Overexpressing the IL-33 Antagonist Soluble IL-1 Receptor-Like-1 Attenuate Endotoxin-Induced Acute Lung Injury," *Am J Respir Cell Mol Biol* 49(4): 552-562.
Nakanishi, W. et al. (2013). "IL-33, but Not IL-25, Is Crucial for the Development of House Dust Mite Antigen-Induced Allergic Rhinitis," *PLoS ONE* 8(10): 1-8.
Qiu, C. et al. (2012). "Anti-interleukin-33 inhibits cigarette smoke-induced lung inflammation in mice," *Immunology* 138: 76-82.
Li, D. et al. (2014). "IL-33 promotes ST2-dependent lung fibrosis by the induction of alternatively activated macrophages and innate lymphoid cells in mice," *J. Allergy Clin Immunol* 134(6): 1422-1432.e11.
Saluja, R. et al. (2015). "The role of the IL-33/IL-1RL1 axis in mast cell and basophil activation in allergic disorders," *Molecular Immunology* 63: 80-85.
Hynes Jr., J. et al. (2014). "Advanced in the Discovery of Small-Molecule IRAK4 Inhibitors," *Annual Reports in Medicinal Chemistry* 49: 117-133.
Baddam, S.R. et al. (2013). "Regioselective methylation of indazoles using methyl 2,2,2-trichloromethylacetimidate," *Tetrahedron Letters* 54: 1661-1663.
Tian, Q. et al. (2013). "A Practical Synthesis of a P13K Inhibitor under Noncryogenic Conditions via Functionalization of Lithium Triarylmagnesiate Intermediate," *Organic Process Research & Development* 17: 97-107.
Slade, D.J. et al. (2009). "Indazoles: Regioselective Protection and Subsequent Amine Coupling Reactions," *J. Org. Chem.* 74: 6331-6334.
Cheung, M. et al. (2003). "Efficient and Regioselective Synthesis of 2-Alkyl-2H-indazoles," *J. Org. Chem.* 68: 4093-4095.
Lin, M-H. et al. (2015). "Regioselective synthesis of 2H-indazoles through Ga/Al-and Al-mediated direct alkylation reaction of indazoles," *Org. Biomol. Chem.* 13: 11376-11381.
Luo, G. et al. (2006). "Regioselective Protection at N-2 and Derivatization at C-3 of Indazoles," *J. Org. Chem.* 71: 5392-5395.
Shumeiko, A.E. et al. (2006). "Regioselectivity in Azoles Alkylation. Benzylation of Indazole under Conditions of the Phase-transfer Catalysis," *Russian Journal of Organic Chemistry* 42(2): 294-295.
Jaffari, G.A. et al. (1973). "Methylation of Indazoles and Related Reactions," *Journal of the Chemical Society* 1: 2371-2374.
Tsypin, V.G. et al. (2002). "Adamantylation of Indazole and its C-Nitro Derivatives," *Russian Journal of Organic Chemistry* 38(1): 90-94.
Jain, S.K. et al. (2012). "KF/alumina catalyzed regioselective benzylation and benzoylation using solvent-free grind-stone chemistry," *RSC Adv.* 2: 8929-8933.
Gavara, L. et al. (2011). "Regioselective synthesis of novel substituted indazole-5,6-diamine derivatives," *Tetrahedron* 67: 1633-1639.
Chakrabarty, M. et al. (2008). "An expedient, regioselective synthesis of novel 2-alkylamino- and 2-alkylthiothiazolo[5,4-e]- and -[4,5-g]indazoles and their anticancer potential," *Tetrahedron* 64: 6711-6723.
Reddy, M.T. et al. (2014). "Synthesis and molecular docking studies of new substituted indazole derivatives for anti-breast cancer activity," *Der Pharma Chemica* 6(6): 411-417.
Haydar, S.N. et al. (2010). "5-Cyclic Amine-3-arylsulfonylindazoles as Novel 5-HT$_6$ Receptor Antagonists," *J. Med. Chem.* 53: 2521-2527.
Chirkova, Z.V. et al. (2012). "Synthesis of Substituted Indazole-5,6-dicarbonitriles," *Russian Journal of Organic Chemistry* 48(12): 1557-1560.
Marminon, C. et al. (2007). "Synthesis of N-benzylated indole-, indazole- and benzotriazole-4,7-diones," *Tetrahedron* 63: 735-739.
Nguyen, T.M. et al. (2014). "Anti-Markovnikov Hydroamination of Alkenes Catalyzed by a Two-Component Organic Photoredox System: Direct Access to Phenethylamine Derivatives," *Angew Chem Int Ed Engl.* 53(24): 6198-6201.

Niedermann, K. et al. (2011). "A Ritter-Type Reaction: Direct Electrophilic Trifluoromethylation at Nitrogen Atoms Using Hypervalent Iodine Reagents," *Angew. Chem. Int. Ed.* 50: 1059-1063.
Salerno, L. et al. (2012). "Novel inhibitors of nitric oxide synthase with antioxidant properties," *European Journal of Medicinal Chemistry* 49: 118-126.
Hunt, K.W. et al. (2009). "Selective Synthesis of 1-Functionalized-alkyl-1H-indazoles$^§$," *Organic Letters* 11(21): 5054-5057.
Yang, J. et al. (2016). "Highly Efficient Synthesis of $N^1$-Substituted 1H-Indazoles by DBU-Catalyzed Aza-Michael Reaction of Indazole with Enones," *Synthesis* 48: 1139-1146.
Kym, P.R. et al. (2006). "Screening for Cardiovascular Safety: A Structure—Activity Approach for Guiding Lead Selection of Melanin Concentrating Hormone Receptor 1 Antagonists," *J. Med. Chem.* 49: 2339-2352.
Souers, A.J. et al. (2005). "Identification of 2-(4-Benzyloxyphenyl)-N-[1-(20pyrrolidin-1 -yl-ethyl)-1H-indazol-6-yl]acetamide, an Orally Efficacious Melanin-Concentrating Hormone Receptor 1 Antagonist for the Treatment of Obesity," *J. Med. Chem.* 48: 1318-1321.
Bethanamudi, P. et al. (2012). "Synthesis of Novel $N^1$ and $N^2$ Indazole Derivatives," *E-Journal of Chemistry* 9(4): 1676-1682.
Palit, S. et al. (2015). "Synthesis of Novel Indazole-Derived Ionic Liquids," *Synthesis* 47: 3371-3384.
Cottet, F. et al. (2003). "Recommendable Routes to Trifluoromethyl-Substituted Pyridine- and Quinolinecarboxylic Acids," *Eur. J. Org. Chem.* 1559-1568.
Ashimori, A. et al. (1990). "Novel 1,4-Dihydropyridine Calcium Antagonists. I. Synthesis and Hypotensive Activity of 4-(Substituted Pyridyl)-1, 4-dihydropyridine Derivatives," *Chem. Pharm. Bull.* 38(9): 2446-2458.
Damasio (1996). "Alzheimer's Disease and Related Dementias," Cecil Textbook of Medicine, 20th Edition, vol. 2, pp. 1992-1996.
Gura, T. (1997). "Systems for identifying new drugs are often faulty," Science 278(5340): 1041-1042.
Johnson, J. et al. (2001). "Relationships between drug activity in NCI preclinical in vitro and in vivo models and early clinical trials," British Journal of Cancer 84(10): 1424-1431.
Layzer (1996). "Degenerative Diseases of the Nervous System," Cecil Textbook of Medicine, 20th Edition, vol. 2, pp. 2050-2057.
Moco, S. et al. (2007). "Metabolomics technologies and metabolite identification," Trends in Analytical Chemistry, 26(9): 855-866.
Pearce, H. et al. (2008). "Failure modes in anticancer drug discovery and development," Cancer Drug Design and Discovery, ed. Stephen Neidle, Chapter 18, 424-435.
Seganish (2016). "Inhibitors of interleukin-1 receptor-associated kinase 4 (IRAK4): a patent review (2012-2015)," Expert Opinion on Therapeutic Patents, 26(8): 917-932.
Simone, J. (1996). "Oncology: Introduction," Cecil Textbook of Medicine, 20th Edition, vol. 1, 1004-1010.
U.S. Appl. No. 16/081,209, filed Aug. 30, 2018, for Bothe et al. (Also published as US20190071432, cited herewith) (U.S. Patent Application is not submitted herewith pursuant to the waiver of 37 C.F.R. § 1.98(a)(2)(iii) issued by the Office dated Sep. 21, 2004.).
U.S. Appl. No. 16/097,067, filed Oct. 26, 2018, for Thaler et al. (Also published as US20190112270, cited herewith) (U.S. Patent Application is not submitted herewith pursuant to the waiver of 37 C.F.R. § 1.98(a)(2)(iii) issued by the Office dated Sep. 21, 2004.).
U.S. Appl. No. 16/097,463, filed Oct. 29, 2018, for Thaler et al. (Also published as US20190144420, cited herewith) (U.S. Patent Application is not submitted herewith pursuant to the waiver of 37 C.F.R. § 1.98(a)(2)(iii) issued by the Office dated Sep. 21, 2004.).
U.S. Appl. No. 16/097,506, filed Oct. 29, 2018, for Thaler et al. (U.S. Patent Application is not submitted herewith pursuant to the waiver of 37 C.F.R. § 1.98(a)(2)(iii) issued by the Office dated Sep. 21, 2004.).
U.S. Appl. No. 16/306,235, filing date unknown, inventor not yet available. (U.S. Patent Application is not submitted herewith pursuant to the waiver of 37 C.F.R. § 1.98(a)(2)(iii) issued by the Office dated Sep. 21, 2004.).
U.S. Appl. No. 16/306,506, filed May 24, 2017, for Rausch et al. (Also published as US20190125736, cited herewith) (U.S. Patent Application is not submitted herewith pursuant to the waiver of 37 C.F.R. § 1.98(a){2}{iii} issued by the Office dated Sep. 21, 2004).

(56) References Cited

OTHER PUBLICATIONS

U.S. Appl. No. 16/377,025, filed Apr. 5, 2019, for Bothe et al. (U.S. Patent Application is not submitted herewith pursuant to the waiver of 37 C.F.R. § 1.98(a)(2)(iii) issued by the Office dated Sep. 21, 2004.).

U.S. Appl. No. 16/428,669, filed May 31, 2019, for Bothe et al. (U.S. Patent Application is not submitted herewith pursuant to the waiver of 37 C.F.R. § 1.98(a)(2)(iii) issued by the Office dated Sep. 21, 2004.).

* cited by examiner

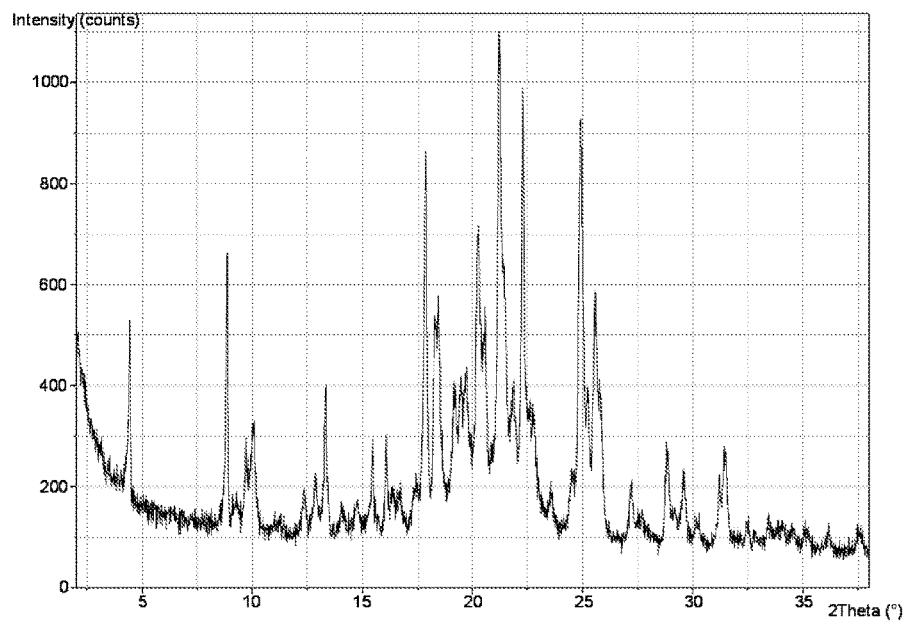
X-Ray powder diffractogram of the polymorphic form B of compound (I)

SYNTHESIS OF INDAZOLES

CROSS REFERENCE TO RELATED APPLICATIONS

This application is a national stage application under 35 U.S.C. § 371 of International Application No. PCT/EP2017/059744, filed internationally on Apr. 25, 2017, which claims the benefit of European Application No. 16167652.3, filed Apr. 29, 2016.

The present invention relates to a novel method of preparing a 2-substituted indazole with the following structure

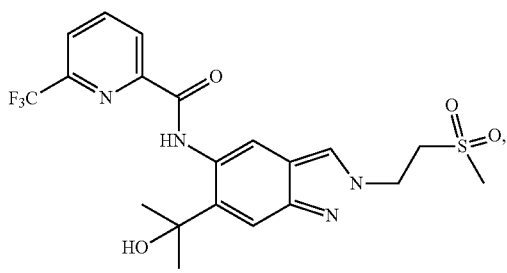

(I)

to a novel polymorphic B form of said 2-substituted indazole, to intermediate compounds, and to the use of intermediate compounds for the preparation of said 2-substituted indazole.

BACKGROUND

The present invention relates to the preparation of substituted indazole of formula (I) which inhibits interleukin-1 receptor-associated kinase 4 (IRAK4).

Human IRAK4 (interleukin-1 receptor-associated kinase 4) plays a key role in the activation of the immune system. Therefore, this kinase is an important therapeutic target molecule for the development of inflammation-inhibiting substances. IRAK4 is expressed by a multitude of cells and mediates the signal transduction of Toll-like receptors (TLR), except TLR3, and receptors of the interleukin (IL)-1β family consisting of the IL-1R (receptor), IL-18R, IL-33R and IL-36R (Janeway and Medzhitov, Annu. Rev. Immunol., 2002; Dinarello, Annu. Rev. Immunol., 2009; Flannery and Bowie, Biochemical Pharmacology, 2010).

Neither IRAK4 knockout mice nor human cells from patients lacking IRAK4 react to stimulation by TLRs (except TLR3) and the IL-1β family (Suzuki, Suzuki, et al., Nature, 2002; Davidson, Currie, et al., The Journal of Immunology, 2006; Ku, von Bernuth, et al., JEM, 2007; Kim, Staschke, et al., JEM, 2007).

The binding of the TLR ligands or the ligands of the IL-1β family to the respective receptor leads to recruitment and binding of MyD88 [Myeloid differentiation primary response gene (88)] to the receptor. As a result, MyD88 interacts with IRAK4, resulting in the formation of an active complex which interacts with and activates the kinases IRAK1 or IRAK2 (Kollewe, Mackensen, et al., Journal of Biological Chemistry, 2004; Precious et al., J. Biol. Chem., 2009). As a result of this, the NF (nuclear factor)-kB signalling pathway and the MAPK (mitogen-activated protein kinase) signal pathway is activated (Wang, Deng, et al., Nature, 2001). The activation both of the NF-kB signalling pathway and of the MAPK signalling pathway leads to processes associated with different immune processes. For example, there is increased expression of various inflammatory signal molecules and enzymes such as cytokines, chemokines and COX-2 (cyclooxygenase-2), and increased mRNA stability of inflammation-associated genes, for example COX-2, IL-6, IL-8 (Holtmann, Enninga, et al., Journal of Biological Chemistry, 2001; Datta, Novotny, et al., The Journal of Immunology, 2004). Furthermore, these processes may be associated with the proliferation and differentiation of particular cell types, for example monocytes, macrophages, dendritic cells, T cells and B cells (Wan, Chi, et al., Nat Immunol, 2006; McGettrick and J. O'Neill, British Journal of Haematology, 2007).

The central role of IRAK4 in the pathology of various inflammatory disorders had already been shown by direct comparison of wild-type (WT) mice with genetically modified animals having a kinase-inactivated form of IRAK4 (IRAK4 KDKI). IRAK4 KDKI animals have an improved clinical picture in the animal model of multiple sclerosis, atherosclerosis, myocardial infarction and Alzheimer's disease (Rekhter, Staschke, et al., Biochemical and Biophysical Research Communication, 2008; Maekawa, Mizue, et al., Circulation, 2009; Staschke, Dong, et al., The Journal of Immunology, 2009; Kim, Febbraio, et al., The Journal of Immunology, 2011; Cameron, Tse, et al., The Journal of Neuroscience, 2012). Furthermore, it was found that deletion of IRAK4 in the animal model protects against virus-induced myocarditis an improved anti-viral reaction with simultaneously reduced systemic inflammation (Valaperti, Nishii, et al., Circulation, 2013). It has also been shown that the expression of IRAK4 correlates with the degree of Vogt-Koyanagi-Harada syndrome (Sun, Yang, et al., PLoS ONE, 2014).

As well as the essential role of IRAK4 in congenital immunity, there are also hints that IRAK4 influences the differentiation of what are called the Th17 T cells, components of adaptive immunity. In the absence of IRAK4 kinase activity, fewer IL-17-producing T cells (Th17 T cells) are generated compared to WT mice. The inhibition of IRAK4 is therefore suitable for prophylaxis and/or treatment of atherosclerosis, type 1 diabetes, rheumatoid arthritis, spondyloarthritis, lupus erythematosus, psoriasis, vitiligo, chronic inflammatory bowel disease and viral disorders, for example HIV (human immunodeficiency virus), hepatitis virus (Staschke, et al., The Journal of Immunology, 2009; Zambrano-Zaragoza, et al., International Journal of Inflammation, 2014).

Owing to the central role of IRAK4 in the MyD88-mediated signal cascade of TLRs (except TLR3) and the IL-1 receptor family, the inhibition of IRAK4 can be utilized for the prophylaxis and/or treatment of disorders mediated by the receptors mentioned. TLRs and also components of the IL-1 receptor family are involved in the pathogenesis of rheumatoid arthritis, metabolic syndrome, diabetes, osteoarthritis, Sjögren syndrome and sepsis (Scanzello, Plaas, et al. Curr Opin Rheumatol, 2008; Roger, Froidevaux, et al, PNAS, 2009; Gambuzza, Licata, et al., Journal of Neuroimmunology, 2011; Fresno, Archives Of Physiology And Biochemistry, 2011; Volin and Koch, J Interferon Cytokine Res, 2011; Akash, Shen, et al., Journal of Pharmaceutical Sciences, 2012; Goh and Midwood, Rheumatology, 2012; Dasu, Ramirez, et al., Clinical Science, 2012; Ramirez and Dasu, Curr Diabetes Rev, 2012; Li, Wang, et al., Pharmacology & Therapeutics, 2013; Sedimbi, Hagglof, et al., Cell Mol Life Sci, 2013; Talabot-Aye, et al., Cytokine, 2014). Skin diseases such as psoriasis, atopic dermatitis, Kindler's syndrome, allergic contact dermatitis, acne inversa and acne vulgaris are associated with the IRAK4-mediated TLR signalling pathway (Gilliet, Conrad, et al., Archives of Dermatology, 2004; Niebuhr, Langnickel, et al., Allergy, 2008; Miller, Adv Dermatol, 2008; Terhorst, Kalali, et al., Am J Clin Dermatol, 2010; Viguier, Guigue, et al., Annals of Internal Medicine, 2010; Cevikbas, Steinhoff, J Invest Dermatol, 2012; Minkis, Aksentijevich, et al., Archives of Dermatology, 2012; Dispenza, Wolpert, et al., J Invest Dermatol, 2012; Minkis, Aksentijevich, et al., Archives of Dermatology, 2012; Gresnigt and van de Veerdonk, Seminars in Immunology, 2013; Selway, Kurczab, et al., BMC Dermatology, 2013; Sedimbi, Hagglof, et al., Cell Mol Life Sci, 2013; Wollina, Koch, et al. Indian Dermatol Online, 2013; Foster, Baliwag, et al., The Journal of Immunology, 2014).

Pulmonary disorders such as pulmonary fibrosis, obstructive pulmonary disease (COPD), acute respiratory distress syndrome (ARDS), acute lung injury (ALI), interstitial lung disease (ILD), sarcoidosis and pulmonary hypertension also show an association with various TLR-mediated signalling pathways. The pathogenesis of the pulmonary disorders may be either infectiously mediated or non-infectiously mediated processes (Ramirez Cruz, Maldonado Bernal, et al., Rev Alerg Mex, 2004; Jeyaseelan, Chu, et al., Infection and Immunity, 2005; Seki, Tasaka, et al., Inflammation Research, 2010; Xiang, Fan, et al., Mediators of Inflammation, 2010; Margaritopoulos, Antoniou, et al., Fibrogenesis & Tissue Repair, 2010; Hilberath, Carlo, et al., The FASEB Journal, 2011; Nadigel, Prefontaine, et al., Respiratory Research, 2011; Kovach and Standiford, International Immunopharmacology, 2011; Bauer, Shapiro, et al., Mol Med, 2012; Deng, Yang, et al., PLoS One, 2013; Freeman, Martinez, et al., Respiratory Research, 2013; Dubaniewicz, A., Human Immunology, 2013). TLRs and also IL-1R family members are also involved in the pathogenesis of other inflammatory disorders such as Behçet's disease, gout, lupus erythematosus, adult-onset Still's disease and chronic inflammatory bowel diseases such as ulcerative colitis and Crohn's disease, and transplant rejection, and so inhibition of IRAK4 here is a suitable therapeutic approach (Liu-Bryan, Scott, et al., Arthritis & Rheumatism, 2005; Christensen, Shupe, et al., Immunity, 2006; Cario, Inflammatory Bowel Diseases, 2010; Nickerson, Christensen, et al., The Journal of Immunology, 2010; Rakoff-Nahoum, Hao, et al., Immunity, 2006; Heimesaat, Fischer, et al., PLoS ONE, 2007; Kobori, Yagi, et al., J Gastroenterol, 2010; Shi, Mucsi, et al., Immunological Reviews, 2010; Leventhal and Schroppel, Kidney Int, 2012; Chen, Lin, et al., Arthritis Res Ther, 2013; Hao, Liu, et al., Curr Opin Gastroenterol, 2013; Kreisel and Goldstein, Transplant International, 2013; Li, Wang, et al., Pharmacology & Therapeutics, 2013; Walsh, Carthy, et al., Cytokine & Growth Factor Reviews, 2013; Zhu, Jiang, et al., Autoimmunity, 2013; Yap and Lai, Nephrology, 2013). Because of the mechanism of action of the compound of formula (I), they are also suitable for prophylactic and/or therapeutic use of the TLR and IL-1R family-mediated disorders endometriosis and atherosclerosis (Akoum, Lawson, et al., Human Reproduction, 2007; Allhorn, Boing, et al., Reproductive Biology and Endocrinology, 2008; Lawson, Bourcier, et al., Journal of Reproductive Immunology, 2008; Seneviratne, Sivagurunathan, et al., Clinica Chimica Acta, 2012; Sikora, Mielczarek-Palacz, et al., American Journal of Reproductive Immunology, 2012; Falck-Hansen, Kassiteridi, et al., International Journal of Molecular Sciences, 2013; Khan, Kitajima, et al., Journal of Obstetrics and Gynaecology Research, 2013; Santulli, Borghese, et al., Human Reproduction, 2013; Sedimbi, Hagglof, et al., Cell Mol Life Sci, 2013).

In addition to the disorders already mentioned, IRAK4-mediated TLR processes have been described in the pathogenesis of eye disorders such as retinal ischaemia, keratitis, allergic conjunctivitis, keratoconjunctivitis sicca, macular degeneration and uveitis (Kaarniranta and Salminen, J Mol Med (Berl), 2009; Sun and Pearlman, Investigative Ophthalmology & Visual Science, 2009; Redfern and McDermott, Experimental Eye Research, 2010; Kezic, Taylor, et al., J Leukoc Biol, 2011; Chang, McCluskey, et al., Clinical & Experimental Ophthalmology, 2012; Guo, Gao, et al., Immunol Cell Biol, 2012; Lee, Hattori, et al., Investigative Ophthalmology & Visual Science, 2012; Qi, Zhao, et al., Investigative Ophthalmology & Visual Science, 2014).

Because of the central role of IRAK4 in TLR-mediated processes, the inhibition of IRAK4 also enables the treatment and/or prevention of cardiovascular and neurological disorders, for example myocardial reperfusion damage, myocardial infarction, hypertension (Oyama, Blais, et al., Circulation, 2004; Timmers, Sluijter, et al., Circulation Research, 2008; Fang and Hu, Med Sci Monit, 2011; Bijani, International Reviews of Immunology, 2012; Bomfim, Dos Santos, et al., Clin Sci (Lond), 2012; Christia and Frangogiannis, European Journal of Clinical Investigation, 2013; Thompson and Webb, Clin Sci (Lond), 2013;), and also Alzheimer's disease, stroke, craniocerebral trauma and Parkinson's disease (Brough, Tyrrell, et al., Trends in Pharmacological Sciences, 2011; Carty and Bowie, Biochemical Pharmacology, 2011; Denes, Kitazawa, Cheng, et al., The Journal of Immunology, 2011; Lim, Kou, et al., The American Journal of Pathology, 2011; Béraud and Maguire-Zeiss, Parkinsonism & Related Disorders, 2012; Denes, Wilkinson, et al., Disease Models & Mechanisms, 2013; Noelker, Morel, et al., Sci. Rep., 2013; Wang, Wang, et al., Stroke, 2013).

Because of the involvement of TLR signals and IL-1 receptor family-mediated signals via IRAK4 in the case of pruritus and pain, for example cancer pain, post-operative pain, inflammation-induced and chronic pain, there may be assumed to be a therapeutic effect in the indications mentioned through the inhibition of IRAK4 (Wolf, Livshits, et al., Brain, Behavior, and Immunity, 2008; Kim, Lee, et al., Toll-like Receptors: Roles in Infection and Neuropathology, 2009; del Rey, Apkarian, et al., Annals of the New York Academy of Sciences, 2012; Guerrero, Cunha, et al., European Journal of Pharmacology, 2012; Kwok, Hutchinson, et al., PLoS ONE, 2012; Nicotra, Loram, et al., Experimental Neurology, 2012; Chopra and Cooper, J Neuroimmune Pharmacol, 2013; David, Ratnayake, et al., Neurobiology of Disease, 2013; Han, Zhao, et al., Neuroscience, 2013; Liu and Ji, Pflugers Arch., 2013; Stokes, Cheung, et al., Journal of Neuroinflammation, 2013; Zhao, Zhang, et al., Neuroscience, 2013; Liu, Y. Zhang, et al., Cell Research, 2014).

This also applies to some oncological disorders. Particular lymphomas, for example ABC-DLBCL (activated B-cell diffuse large-cell B-cell lymphoma), mantle cell lymphoma and Waldenström's disease, and also chronic lymphatic leukaemia, melanoma and liver cell carcinoma, are characterized by mutations in MyD88 or changes in MyD88 activity which can be treated by an IRAK4 inhibitor (Ngo, Young, et al., Nature, 2011; Puente, Pinyol, et al., Nature, 2011; Srivastava, Geng, et al., Cancer Research, 2012; Treon, Xu, et al., New England Journal of Medicine, 2012; Choi, Kim, et al., Human Pathology, 2013; (Liang, Chen, et al., Clinical Cancer Research, 2013). In addition, MyD88 plays an important role in ras-dependent tumours, and so IRAK4 inhibitors are also suitable for treatment thereof (Kfoury, A., K. L. Corf, et al., Journal of the National Cancer Institute, 2013).

Inflammatory disorders such as CAPS (cryopyrin-associated periodic syndromes) including FCAS (familial cold autoinflammatory syndrome), MWS (Muckle-Wells syndrome), NOMID (neonatal-onset multisystem inflammatory disease) and CONCA (chronic infantile, neurological, cutaneous, and articular) syndrome; FMF (familial mediterranean fever), HIDS (hyper-IgD syndrome), TRAPS (tumour necrosis factor receptor 1-associated periodic syndrom), juvenile idiopathic arthritis, adult-onset Still's disease, Adamantiades-Behçet's disease, rheumatoid arthritis, osteoarthritis, keratoconjunctivitis sicca and Sjögren syndrome are treated by blocking the IL-1 signal pathway; therefore here, too, an IRAK4 inhibitor is suitable for treatment of the diseases mentioned (Narayanan, Corrales, et al., Cornea, 2008; Henderson and Goldbach-Mansky, Clinical Immunology, 2010; Dinarello, European Journal of Immunology, 2011; Gul, Tugal-Tutkun, et al., Ann Rheum Dis, 2012; Pettersson, Annals of MedicinePetterson, 2012; Ruperto, Brunner, et al., New England Journal of Medicine, 2012; Nordstrom, Knight, et al., The Journal of Rheumatology, 2012; Vijmasi, Chen, et al., Mol Vis, 2013; Yamada, Arakaki, et al., Opinion on Therapeutic Targets, 2013). The ligand of IL-33R, IL-33, is involved particularly in the pathogenesis of acute kidney failure, and so the inhibition of IRAK4 for prophylaxis and/or treatment is a suitable therapeutic approach (Akcay, Nguyen, et al., Journal of the American Society of Nephrology, 2011). Components of the IL-1 receptor family are associated with myocardial infarction, different pulmonary disorders such as asthma, COPD, idiopathic interstitial pneumonia, allergic rhinitis, pulmonary fibrosis and acute respiratory distress syndrome (ARDS), and so prophylactic and/or therapeutic action is to be expected in the indications mentioned through the inhibition of IRAK4 (Kang, Homer, et al., The Journal of Immunology, 2007; Imaoka, Hoshino, et al., European Respiratory Journal, 2008; Couillin, Vasseur, et al., The Journal of Immunology, 2009; Abbate, Kontos, et al., The American Journal of Cardiology, 2010; Lloyd, Current Opinion in Immunology, 2010; Pauwels, Bracke, et al., European Respiratory Journal, 2011; Haenuki, Matsushita, et al., Journal of Allergy and Clinical Immunology, 2012; Yin, Li, et al., Clinical & Experimental Immunology, 2012; Abbate, Van Tassell, et al., The American Journal of Cardiology, 2013; Alexander-Brett, et al., The Journal of Clinical Investigation, 2013; Bunting, Shadie, et al., BioMed Research International, 2013; Byers, Alexander-Brett, et al., The Journal of Clinical Investigation, 2013; Kawayama, Okamoto, et al., J Interferon Cytokine Res, 2013; Martínez-González, Roca, et al., American Journal of Respiratory Cell and Molecular Biology, 2013; Nakanishi, Yamaguchi, et al., PLoS ONE, 2013; Qiu, Li, et al., Immunology, 2013; Li, Guabiraba, et al., Journal of Allergy and Clinical Immunology, 2014; Saluja, Ketelaar, et al., Molecular Immunology, 2014).

The prior art discloses a multitude of IRAK4 inhibitors (see, for example, Annual Reports in Medicinal Chemistry (2014), 49, 117-133).

U.S. Pat. No. 8,293,923 and US20130274241 disclose IRAK4 inhibitors having a 3-substituted indazole structure. There is no description of 2-substituted indazoles.

WO2013/106254 and WO2011/153588 disclose 2,3-disubstituted indazole derivatives.

WO2007/091107 describes 2-substituted indazole derivatives for the treatment of Duchenne muscular dystrophy. The compounds disclosed do not have 6-hydroxyalkyl substitution.

WO2015/091426 describes indazoles, the alkyl group thereof substituted at position 2 by a carboxamide structure.

WO2015/104662 disloses indazole compounds of formula (I)

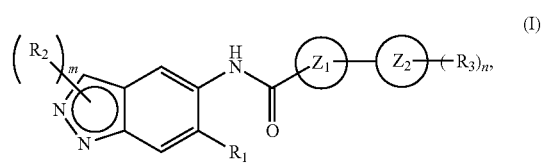

which are therapeutically useful as kinase inhibitor, particularly IRAK4 inhibitors, and pharmaceutically acceptable salts or stereoisomers thereof that are useful in the treatment and prevention of diseases or disorder, in particular their use in diseases or disorder mediated by kinase enzyme, particularly IRAK4 enzyme.

WO2016/083433, published after the priority date of the present application, describes novel substituted indazoles of the following formula

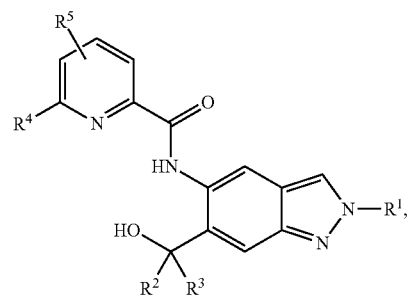

methods for the production thereof, use thereof alone or in combinations to treat and/or prevent diseases, and use thereof to produce drugs for treating and/or preventing diseases, in particular for treating and/or preventing endometriosis and endometriosis-associated pain and other symptoms associated with endometriosis such as dysmenorrhea, dyspareunia, dysuria, and dyschezia, lymphomas, rheumatoid arthritis, spondyloarthritides (in particular psoriatic spondyloarthritis and Bekhterev's disease), lupus erythematosus, multiple sclerosis, macular degeneration, COPD, gout, fatty liver diseases, insulin resistance, tumor diseases, and psoriasis.

The novel IRAK4 inhibitor shall be especially suitable for treatment and for prevention of proliferative and inflammatory disorders characterized by an overreacting immune system. Particular mention should be made here of inflammatory skin disorders, cardiovascular disorders, lung disorders, eye disorders, autoimmune disorders, gynaecological disorders, especially endometriosis, and cancer.

A process was to be disclosed that would allow the production of indazole (I) on technical scale with special focus on the following requirements:

Scale-up/scalability of the manufacturing process

High regioselectivity in the N2-alkylation reaction

Avoidance of chromatographic separation and purification steps

Final processing via crystallization

Final adjustment of the polymorphic form using Class 3 solvents (in accordance with FDA guidelines)

Remarkably, a process could be disclosed that meets all of the requirements mentioned above. This invention describes the preparation of compound (I) via a surprisingly highly selective alkylation on N2:

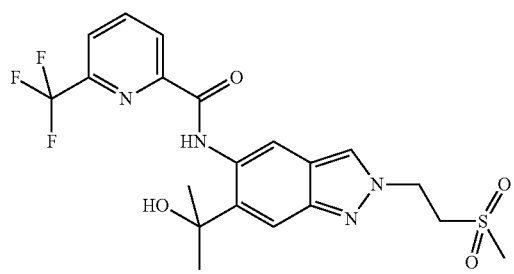

(I)

Preparations of N2-substituted indazoles have been previously described in the literature. These procedures, however, have considerable disadvantages rendering them unsuitable for technical scale. It is possible to selectively prepare N2-substituted indazoles via complex sequences of synthetic steps, which involve no direct alkylation step. These sequences, however, are long and tedious and involve considerable losses ultimately resulting in a low total yield. Therefore, synthetic routes which allow a direct preparation of N2-substituted indazoles from 1H-indazole precursors via direct and selective alkylation at N2 are most interesting. At the attempt of directly alkylating the 1H-indazole precursor of the general formula (II), generally a mixture made up of the N1- (IIIa) and N2-alkylated (III) regioisomers is obtained.

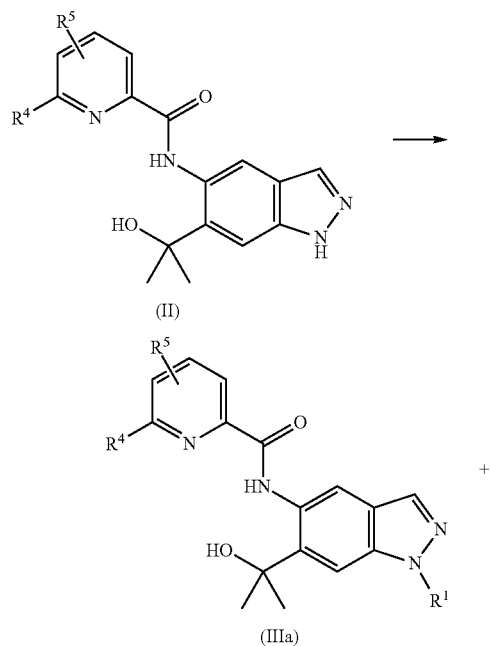

Indazole and its derivatives, a typical class of aromatic N-heterocycles, have sparked significant interest in synthetic and medicinal chemistry due to their diverse biological activities. Furthermore, diverse heterocyclic structures could be accessed from indazole-derived N-heterocyclic carbenes. Among indazoles, N1/N2-substituted indazoles are widely used as anticancer, anti-inflammatory, anti-HIV, and antimicrobial drugs. Generally, the synthesis of N2-substituted indazoles involves cyclization procedures from miscellaneous starting materials. Unfortunately, general methodologies remain scarce in the literature. Therein, only moderate yields were obtained.

With respect to the current state of technology, several publications are known and will be discussed in the following section. None of the published procedures feature reaction conditions that lead to a direct N2-selective alkylation using methyl vinyl sulfone as alkylating agent. There is either no conversion observed or the selectivity and yield are low. The problem of the prior art procedures consists in the use of relatively simple alkylating agents bearing no labile functional groups. These agents are mostly attached to the 1H-indazole via nucleophilic substitution of their halides, tosylates, triflates or mesylates. When more functionalized moieties are used, yield and selectivity decrease dramatically. In the following section, the reasons are presented why these prior art procedures are not applicable to the challenge at hand:

1. WO 2011/043479: The reactions are carried out in THF at reflux (see scheme 2). This does not work for the case at hand (methyl vinyl sulfone). The preparation of the corresponding triflate from e.g. the alcohol is not possible, as its decomposition occurs instantly. In addition, only a simple substrate with no functionality in the side-chain was used.
2. S. R. Baddam, N. U. Kumar, A. P. Reddy, R. Bandichhor, *Tetrahedron Lett.* 2013, 54, 1661: Only simple indazoles without functional groups were used in the reaction. Only methyl trichloroacetimidate was used as alkylating agent. Attempts to transfer acid-catalyzed conditions to the selective introduction of a methyl ethyl sulfone side chain at the N2 position of an indazole core structure via reaction with methyl vinyl sulfone failed. This procedure cannot easily be scaled up.
3. Q. Tian, Z. Cheng, H. H. Yajima, S. J. Savage, K. L. Green, T. Humphries, M. E. Reynolds, S. Babu, F. Gosselin, D. Askin, Org. *Process Res. Dev.* 2013, 17, 97: The preparation of a THP-ether with preference for N2 of the indazole is presented. This reaction proceeds via a different mechanism and does not represent a general method, since the THP-ether product cannot be easily converted further. Furthermore, selective methods for protection of indazoles using p-methoxybenzyl derivatives under acidic conditions are presented. Attempts to transfer these conditions to the selective introduction of a methyl ethyl sulfone side at the N2 position of an indazole core structure via reaction with methyl vinyl sulfone failed.

4. D. J. Slade, N. F. Pelz, W. Bodnar, J. W. Lampe, P. S. Watson, *J. Org. Chem.* 2009, 74, 6331: THP-ether and PMB-protection using acidic conditions (PPTS: pyridinium para-toluenesulfonate), see scheme 2; attempts to transfer these conditions to selective introduction of a methyl ethyl sulfone side chain at the N2 position of an indazole core structure via reaction with methyl vinyl sulfone failed.

5. M. Cheung, A. Boloor, J. A. Stafford, *J. Org. Chem.* 2003, 68, 4093: Highly reactive and highly carcinogenic Meerwein salts were used as alkylating agents (see scheme 2). This method only comprises simple non-functionalized ethyl and methyl Meerwein salts. The reaction proceeds in polar ethyl acetate at ambient temperature. These conditions could not be transferred to selective introduction of a methyl ethyl sulfone side chain at the N2 position of an indazole core structure via reaction with methyl vinyl sulfone.

Scheme 1: N-alkylation of 1H-indazoles

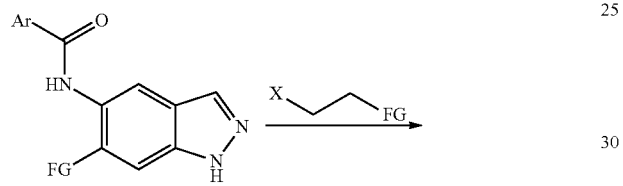

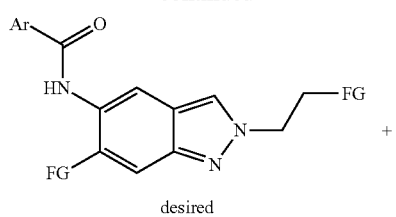

desired

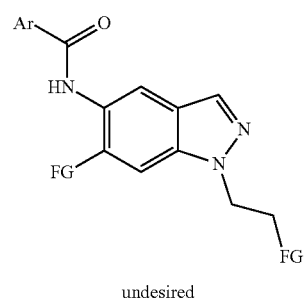

undesired

Scheme 2: N-alkylation methods of indazoles known from prior art

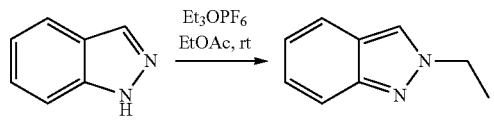

*JOC* 2003, 4093

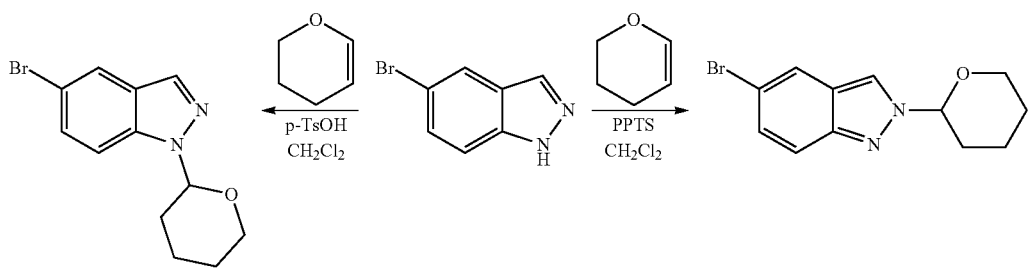

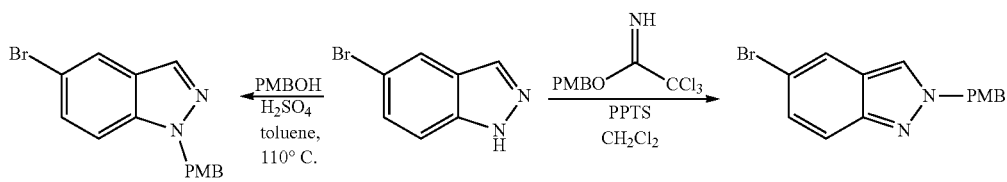

*JOC* 2009, 6331

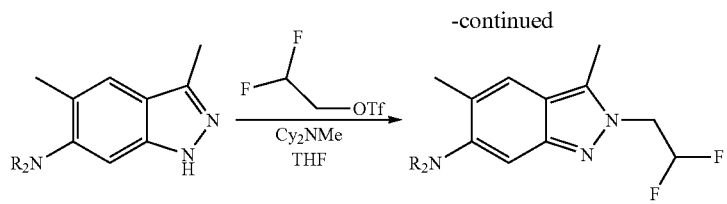

PCT Int. Appl., 2011043479 p-TsOH: p-toluenesulfonic acid
PPTS: Pyridinium p-toluenesulfonate
PMB: p-methoxybenzyl 6. M.-H. Lin, H.-J. Liu, W.-C. Lin, C.-K. Kuo, T.-H. Chuang, *Org. Biomol. Chem.* 2015, 13, 11376: The procedure is N2-selective; however, it cannot be scaled up with Ga and Al metal being used in stoichiometric amounts. Under the described reaction conditions, Broensted acids are formed which react with the corresponding metals to give hydrogen gas. Only relatively simple substrates are used as alkylating agents (no sulfone group). When more functionalized substrates were used, a significant decrease in yield was observed. Attempts to transfer these conditions to selective introduction of a methyl ethyl sulfone side chain at the N2 position of an indazole core structure via reaction with methyl vinyl sulfone failed.

7. G. Luo, L. Chen, G. Dubowchick, *J. Org. Chem.* 2006, 71, 5392: 2-(Trimethylsilyl)ethoxymethyl chloride (SEM-Cl) in THF was used for substitution on N2 of indazoles. Attempts to transfer these conditions to selective introduction of a methyl ethyl sulfone side chain at the N2 position of an indazole core structure via reaction with methyl vinyl sulfone failed. The corresponding products described in this publication are ethers and are not related to our target molecule. The use of highly carcinogenic 2-(trimethylsilyl)ethoxymethyl chloride (SEM-Cl) as well as benzyloxymethyl chloride (BOM-Cl) does not represent a scalable option for obtaining the target compound.

8. A. E. Shumeiko, A. A. Afon'kin, N. G. Pazumova, M. L. Kostrikin, *Russ. J. Org. Chem.* 2006, 42, 294: Only very simple substrates were used in this method. No significant selectivity is reported. A slight preference for N1-alkylation at the indazole was observed.

9. G. A. Jaffari, A. J. Nunn, *J. Chem. Soc. Perkin* 1 1973, 2371: Very simple substrates and only methylation agents were used. A more complex substrate as e.g. a combination of formaldehyde with protonated methanol resulted in only N1-substituted product (ether).

10. V. G. Tsypin et al., *Russ. J. Org. Chem.* 2002, 38, 90: The reaction proceeds in sulfuric acid and chloroform. Only conversions of simple indazoles with adamanthyl alcohol as sole alkylating agent are described. These conditions could not be transferred to the selective introduction of a methyl ethyl sulfone side chain at the N2 position of an indazole core structure via reaction with methyl vinyl sulfone.

11. S. K. Jains et al. *RSC Advances* 2012, 2, 8929: This publication features an example of N-benzylation of indazoles with low selectivity towards N1-substitution. This KF-/alumina-catalyzed method cannot be used efficiently for the synthesis of N2-substituted indazoles. Attempts to transfer these conditions to selective introduction of a methyl ethyl sulfone side chain at the N2-position of an indazole core structure via reaction with methyl vinyl sulfone failed.

12. L. Gavara et al. *Tetrahedron* 2011, 67, 1633: Only relatively simple substrates were used. The described acidic THP-ether formation and benzylation in refluxing THF are not applicable to our substrate. Attempts to transfer these conditions to selective introduction of a methyl ethyl sulfone side chain at the N2-position of an indazole core structure via reaction with methyl vinyl sulfone failed.

13. M. Chakrabarty et al. *Tetrahedron* 2008, 64, 6711: N2-alkylation was observed but N1-alkylated product was obtained preferentially. The described conditions of using aqueous sodium hydroxide and phase transfer catalyst in THF are not applicable to 2-substituted indazoles. Attempts to transfer these conditions to our system (methyl vinyl sulfone) failed.

14. M. T. Reddy et al. *Der Pharma Chemica* 2014, 6, 411: The reaction proceeds in the corresponding alkylating agent as solvent. Only the use of highly reactive ethyl bromoacetate as alkylating agent is reported. There are no data on the selectivity. These conditions are not applicable to a selective synthesis of N2-substituted indazoles. Attempts to transfer these conditions to selective introduction of a methyl ethyl sulfone side chain at the N2 position of an indazole core structure via reaction with methyl vinyl sulfone failed.

15. S. N. Haydar et al. *J. Med. Chem.* 2010, 53, 2521: Only simple non-functionalized alkyl groups are described (methyl, isopropyl, isobutyl). Cesium carbonate was used as base and the reaction resulted in a mixture of N1- and N2-alkylated products. These conditions are not applicable to compounds as 2-indazoles. Attempts to transfer these conditions to selective introduction of a methyl ethyl sulfone side chain at the N2-position of an indazole core structure via reaction with methyl vinyl sulfone failed.

16. Zh. V. Chirkova et al. *Russ. J. Org. Chem.* 2012, 48, 1557: In this method, relatively simple substrates are converted with potassium carbonate as base in DMF. Mixtures of N1- and N2-alkylated products are obtained. The conditions are not applicable to a selective synthesis of N2-substituted indazoles. Attempts to transfer these conditions to selective introduction of a methyl ethyl sulfone side chain at the N2-position of an indazole core structure via reaction with methyl vinyl sulfone failed.

17. C. Marminon et al. *Tetrahedron* 2007, 63, 735: The ortho-substituent R in position 7 at the indazole directs the alkylation towards N2 via shielding N1 from electrophilic attacks. The conditions, sodium hydride as base in THF, are not applicable to a selective synthesis of N2-substituted indazoles as they preferentially result in alkylation at N1 in absence of a substituent in position 7 of the indazole. Attempts to transfer these conditions to selective introduction of a methyl ethyl sulfone side chain at the N2-position of an indazole core structure via reaction with methyl vinyl sulfone failed.
18. D. A. Nicewicz et al. *Angew. Chem. Int. Ed.* 2014, 53, 6198: Only simple substrates were used. This method describes a photochemical reaction that cannot easily be scaled up and is not applicable to a general, selective synthesis of N2-substituted indazoles Very specific styrene derivatives are used under radical reaction conditions. Attempts to transfer these conditions to selective introduction of a methyl ethyl sulfone side chain at the N2-position of an indazole core structure via reaction with methyl vinyl sulfone failed.
19. A. Togni et al. *Angew. Chem. Int. Ed.* 2011, 50, 1059: This publication solely describes a special type of substituent (hypervalent iodine as trifluoromethylation reagent in combination with acetonitrile). This special case is not applicable to a general, selective synthesis of N2-substituted indazoles.
20. L. Salerno et al. *European J. Med. Chem.* 2012, 49, 118: This publication describes the conversion of indazoles in an α-bromoketone melt. The reaction conditions cannot be transferred to a selective synthesis of N2-substituted indazoles. Attempts to transfer these conditions to the selective introduction of a methyl ethyl sulfone side chain at the N2-position of an indazole core structure via reaction with methyl vinyl sulfone failed.
21. K. W. Hunt, D. A. Moreno, N. Suiter, C. T. Clark, G. Kim, *Org. Lett.* 2009, 11, 5054: This publication essentially describes an N1-selective alkylation method with addition of different bases. Simple substrates were used. Attempts to transfer these conditions to the selective introduction of a methyl ethyl sulfone side chain at the N2-position of an indazole core structure via reaction with methyl vinyl sulfone failed.
22. J. Yang et al. *Synthesis* 2016, 48, 48, 1139: This publication describes an N1-selective base-catalyzed aza-Michael reaction. No substitution at N2 was observed. Attempts to transfer these conditions to the selective introduction of a methyl ethyl sulfone side chain at the N2-position of an indazole core structure via reaction with methyl vinyl sulfone failed.
23. P. R. Kym et al. *J. Med. Chem.* 2006, 49, 2339: Essentially N1-alkylations are described. Attempts to transfer these conditions to selective introduction of a methyl ethyl sulfone side chain at the N2-position of an indazole core structure via reaction with methyl vinyl sulfone failed.
24. A. J. Souers et al. *J. Med. Chem.* 2005, 48, 1318: This publication also describes the use of potassium carbonate as base. This method proceeds mainly with preference for substitution at N1 and is therefore not applicable to a selective synthesis of N2-substituted indazoles. Attempts to transfer these conditions to selective introduction of a methyl ethyl sulfone side chain at the N2-position of an indazole core structure via reaction with methyl vinyl sulfone failed.
25. P. Bethanamudi et al. *E-Journal of Chemistry* 2012, 9, 1676: The use of ionic liquids along with potassium carbonate as base results in mixtures of N1- and N2-alkylated indazoles with low yields. The selectivity shows a tendency towards substitution at N1. The use of ionic liquid cannot be transferred to our system. Attempts to transfer these conditions to selective introduction of a methyl ethyl sulfone side chain at the N2-position of an indazole core structure via reaction with methyl vinyl sulfone failed.
26. S. Palit et al. *Synthesis* 2015, 3371: The reaction described herein is essentially non-selective with a slight preference of substitution at N1 of the indazole. Only simple, non-functionalized alkyl groups were used. Sodium hydride and similarly strong bases were used. Attempts to transfer these conditions to selective introduction of a methyl ethyl sulfone side chain at the N2 position of an indazole core structure via reaction with methyl vinyl sulfone failed.

BRIEF SUMMARY

It was shown that the compound of the formula (I) can be synthesized analogously to methods previously published in the literature via e.g. direct alkylation using 2-bromoethyl methyl sulfone. However, a mixture of N1- and N2-alkylated products was obtained with a preference for the N1-regioisomer (N1: N2=ca. 2:1). Desired N2-alkylated indazole of formula (I) could also be obtained in a very low yield as described in WO2016/083433, published after the priority date of the present application, with the following reaction procedure:

160 mg (0.44 mmol) of N-[6-(2-hydroxypropan-2-yl)-1H-indazol-5-yl]-6-(trifluoromethyl)pyridine-2-carboxamide (Intermediate 5-1) were suspended together with 182 mg of potassium carbonate and 36 mg of potassium iodide in 1.0 ml of DMF, and the mixture was stirred at room temperature for 15 min. Then, 123 mg of 2-bromoethyl methyl sulfone were added and the mixture was stirred at room temperature overnight. Water was added, the mixture was extracted twice with ethyl acetate and the extracts were washed with saturated aqueous sodium chloride solution, filtered through a hydrophobic filter and concentrated. Purification of the residue by preparative HPLC gave 20 mg (9.7% yield) of the title compound.

Consumptive preparative HPLC proved indispensable for an efficient separation of the N1-/N2-regioismers. The aim of this new inventive process consists in avoiding HPLC separation via achieving a better selectivity in the reaction in favour of substitution at N2 followed by a new inventive recrystallization procedure.

DESCRIPTION OF THE FIGURES

FIG. 1 shows the X-Ray powder diffractogram (at 25° C. and with Cu—K alpha 1 as radiation source) of the compound of formula (I) in the polymorphic form B.

DETAILED DESCRIPTION

The present invention provides a process for preparing compounds of the general formula (III) from compounds of the general formula (II)

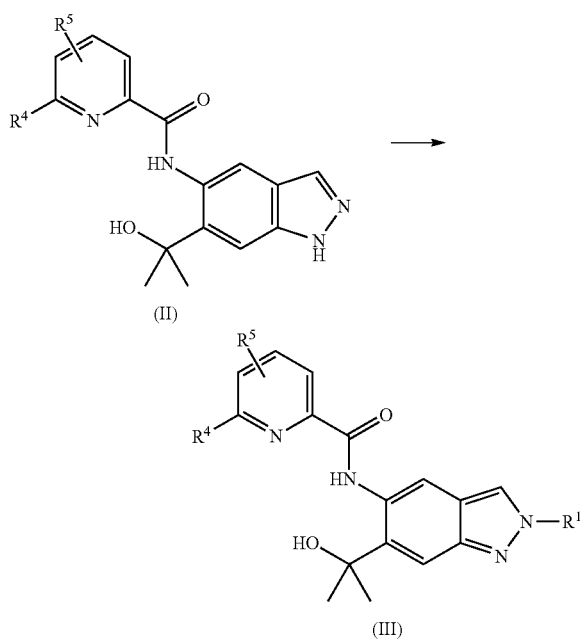

in which
R[1] 2-(methylsulfonyl)ethyl;
R[4] is difluoromethyl, trifluoromethyl or methyl; and
R[5] is hydrogen or fluorine;
with preferably R[4]=trifluoromethyl and R[5]=H:

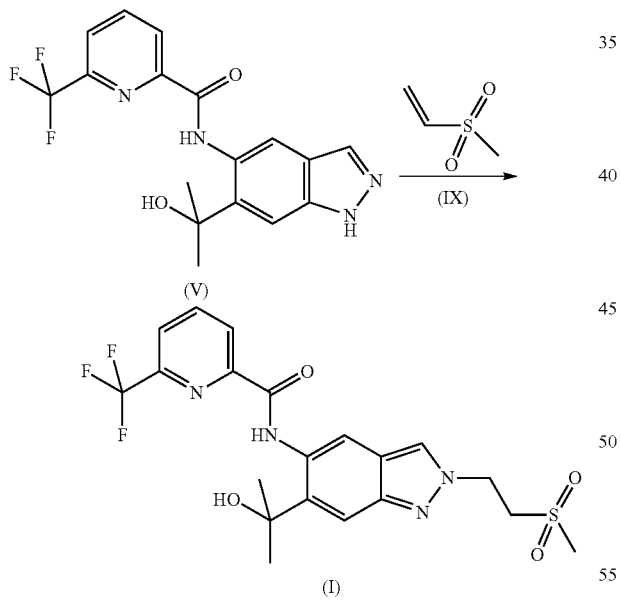

Unexpectedly, we found that methyl vinyl sulfone (IX) can replace the corresponding alkyl halide in the reaction. The use of vinyl sulfones for alkylation of indazoles at N2 is surprisingly unprecedented and therefore highly inventive. Upon reaction of compounds of the general formula (II) with methyl vinyl sulfone in toluene, optionally with addition of an organic base, such as N,N-diisopropylethylamine or triethylamine, the desired N2-isomer according to formulas (III) and (I) is obtained with very high selectivity. The selectivity in the reaction mixture was found to be in between 8:1 to 10:1 in favor of the N2-alkylated product (III) as well as (I). The undesired N1-substituted by-product remained mainly in the mother liquor after work-up of the reaction mixture (mostly <2% after crystallization).

The reaction works without the use of an additional base. The compound of the general formula (II) or (V) is placed in a reaction vessel. 1-2 equivalents of methyl vinyl sulfone are added and the reaction mixture is heated at reflux in toluene (ca. 110° C. internal temperature). The reaction can be performed using 5 to 30 volumes of toluene relative to the amount of starting material (II) or (V). Preferably, the reaction is run with 8 to 15 volumes and best with 10 volumes of toluene. The time of the reaction spans 12 to 100 h. It is run preferably between 48 to 72 h. In some cases, it has proven advantageous to add the methyl vinyl sulfone in portions to the reaction mixture, e.g. start with 1 equivalent and then add 0.3 equivalents after 24 h and further 0.3 equivalents after 48 h. Optionally, the reaction works with catalytic amounts of an organic auxiliary base, e.g. N,N-diisopropylethylamine. The compound of the general formula (II) or (V) is placed in a reaction vessel along with the solvent (toluene or xylene) and catalytic amounts of an organic base.

An auxiliary organic base, e.g. N,N-diisopropylethylamine, N,N-dicyclohexylamine or triethylamine can be added with amounts between 0.01 and 1 equivalent. The reaction proceeds with 0.01 to 0.1 equivalents of base.

It is noteworthy and certainly surprising that using chloro- or ethylbenzene as solvent at the same reaction temperature or xylene as solvent at higher reaction temperature, alkene (IV) was obtained in higher amounts via elimination of water. Strikingly, this elimination was observed in only very small amounts when toluene was used as solvent. Therefore, toluene must be considered as an inventive solvent with unique and completely unanticipated properties regarding this specific reaction. The formation of (IV) was also found to depend on the quality of (V). When (V) was used that had a higher than usual water content (1 wt % instead of <0.5 wt %), a more significant amount of (IV) was obtained in the reaction. It is noteworthy, that formation of the elimination product (VI) can be efficiently suppressed by removing excess water from (V) via azeotropic distillation with toluene and by addition of catalytic amounts of an organic base, in particular N,N-diisopropylethylamine.

(IV)

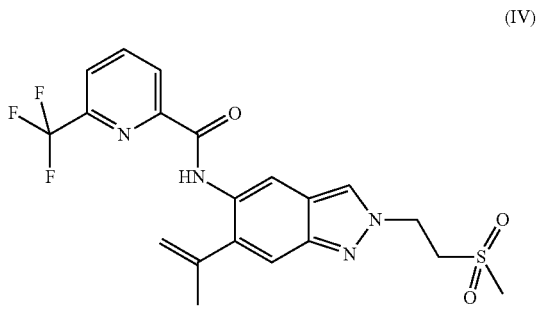 [SMILES: C=C(C)c1cc2nn(CCS(C)(=O)=O)cc2cc1NC(=O)c1cccc(C(F)(F)F)n1]

Isolation procedure: After completion of the reaction, toluene can be partly distilled off the reaction mixture. Subsequently, a second solvent, such as methyl tert-butyl ether (MTBE) or diisopropylether (preferably methyl tert-butyl ether) can be added to the reaction mixture. Upon addition of the respective solvent, the product precipitates almost quantitatively from the mixture. In some cases, it proved useful to seed the mixture with small amounts of crystals in order to obtain a reproducible crystallization. After cooling and prolonged stirring of the resulting suspension, the product is isolated via filtration, washed with solvent and dried at 50 to 60° C. under vacuum resulting typically in 59 to 67% yield. The purity of the crude product typically amounts to 95 to 97% (area) with less than 2% (area) of N1-regioisomer.

It must be emphasized that the reaction of a substituted vinyl sulfone for a directed highly selective preparation of N2-functionalized indazoles is novel, without precedence in the literature and therefore a scientifically highly significant invention for the preparation of such substitution patterns. The preparation of GMP material, which will also be used in clinical trials, requires an additional purification step. Moreover, since the active pharmaceutical ingredient will be used for production of a pharmaceutical composition, such as a tablet, a procedure is required that reproducibly furnishes the identical crystal habit. Surprisingly, this could be realized using ethanol or isopropanol as solvent for recrystallization. Ethanol is the preferred solvent. The compound is therefore first dissolved in acetone and subsequently passed through a particle filter (GMP filtration). Then, a solvent swap from acetone to ethanol is performed via distillation. Distillation is continued until a final volume of 6 to 7 volumes of ethanol relative to the input material is reached. The distillation is cancelled when the boiling point of ethanol has been reached (ca. 77-78° C.) ensuring that all acetone was distilled off. The mixture is then cooled, stirred and the crystallized product is isolated via filtration and dried under vacuum at elevated temperature. The yield of the crystallization is typically >90%. Product that is obtained from this crystallization procedure possesses the desired polymorphism properties required for preparation of a pharmaceutical composition, such as a tablet. The product displays a very high purity as well as a very high content. The most important analytical data for typical batches are given in Table 1:

TABLE 1

Analytical data of batches examples as shown in Table 7

| Purity (HPLC) | ≥99% (area) |
| Content (assay for use) | ≥97.7% (weight) |
| Ethanol | <0.25% (weight) |
| Pd | <1 ppm |

The polymorph obtained via the above described crystallization procedure displays good stability during storage. It can also be easily micronized without losing its crystal properties.

The preparation of compounds according to the general formula (II) as well as (V) is described in WO 2015/091426. This new inventive process focuses on the compound shown by formula (V):

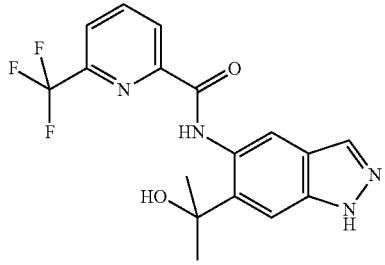

(V)

In the published patent application WO 2015/091426, the compound according to formula (V) is prepared via reaction of the methyl ester compound according to formula (VI):

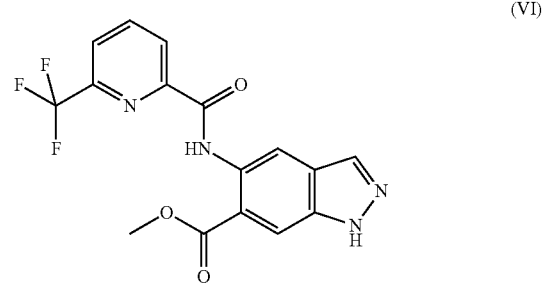 [SMILES: COC(=O)c1cc2[nH]ncc2cc1NC(=O)c1cccc(C(F)(F)F)n1]

(VI)

using a solution of methylmagnesium bromide in diethylether. After work-up, the crude product is subjected to a column chromatographic purification furnishing compound according to formula (V) in 45% yield.

WO2016/083433, published after the priority date of the present application, describes a synthesis route for the preparation of the compound according to formula (V) as well, starting from the compound according to formula (VI) by a Grignard reaction by using suitable alkylmagnesium halides, for example methylmagnesium chloride or methylmagnesium bromide in THF or in diethyl ether or else in mixtures of THF and diethyl ether.

This procedure is not suitable for production of the compound of formula (V) on technical scale due to the following drawbacks:

- The use of diethylether must be avoided due to its low ignition point and its highly explosive potential.
- The relatively costly methylmagnesium bromide was used instead of the more common methylmagnesium chloride, which is easier to procure.
- Chromatographic separations should be avoided on technical scale as they usually require a massive uneconomical consumption of organic solvents.
- No crystallization procedure has been described. According to the usual practice in research laboratories, the compound of formula (V) was evaporated until dryness. This operation is not feasible on technical scale.
- The yield is unsatisfactory: for technical purposes, a yield of at least 75% should be achieved.

Surprisingly, it was found that the compound of formula (V) could be prepared with a significantly higher yield when methylmagnesium chloride and lithium chloride (2:1) in THF were used instead. The reactions proceeded with less byproducts which, using the method described in WO 2015/091426 and WO2016/083433 as well, had to be removed via tedious column chromatography. The reaction was found to proceed best with THF as solvent. 6 to 10 equiv. methylmagnesium chloride (ca. 3 M in THF) and 3 to 5 equivalents lithium chloride are stirred and kept at −10 to 0° C. Within 1 to 3 h, preferably 2 h, the compound according to formula (VI) is dropped to the mixture as solution in THF. The reaction mixture is stirred for 5 to 30 min at the indicated temperature range (−10° C. to 0° C.) and subsequently quenched by being poured into water. The resulting mixture is stirred vigorously. The pH of the mixture is then adjusted to app. 4 via addition of a mineral or organic acid (preferably citric acid) and ethyl acetate is added. Phases were separated and the organic phase was washed several times with brine (aqueous sodium chloride solution). The resulting organic solution was subjected to a solvent swap with toluene via distillation. During this process, the compound according to formula (V) started to crystallize and could be isolated via filtration. The precipitate was dried at elevated temperature (50-60° C.) under vacuum. Typically, yields at this stage were in the range of 80 to 96% and purities between 95 to 99 area % (HPLC).

For the preparation of material with current good manufacturing practice (cGMP) quality, it proved beneficial to finally stir this product in a mixture of isopropanol/water (1:1; 2 to 10 volumes relative to input material). The material is stirred for 1 to 5 h, preferably 3 h. It is then filtrated and washed twice with small amounts of a 1:1 isopropanol/water mixture. The product is dried at elevated temperature (50-60° C.) under vacuum. Typically, yields >90% and purities >97 area % (HPLC) are achieved.

In the following examples in the experimental section, a variant (see example #2, variant #3) is also described in which, after treatment with activated charcoal, a solvent swap directly to isopropanol is performed. The product is crystallized by addition of water. In this way, the product is directly obtained with very high purity.

The preparation of the compound according to formula (VI) has also been described in the patent application WO 2015/091426. Thereby, 6-(trifluoromethyl)pyridine-2-carboxylic acid (VII) (CAS no.: 21190-87-4) was coupled with the aniline-like compound of formula (VIII) (methyl-5-amino-1H-indazol-6-carboxylate; CAS no.: 1000373-79-4) using 1-[bis(dimethylamino)methylene]-1H-1,2,3-triazolo[4,5-b]pyridinium 3-oxid hexafluorophosphate (CAS no.: 148893-10-1) as coupling agent. Amide (VI) was obtained with 84% yield.

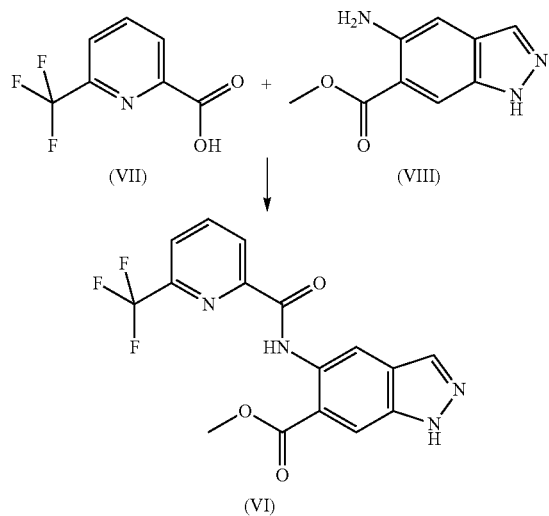

Due to process safety reasons, an up-scaling of uronium-based coupling reagents is not possible because of their explosive potential. Therefore, an alternative coupling method had to be found. The safe and scalable method for the preparation of amide-like compound of formula (VI) is based on the use of T3P (2,4,6-tripropyl-1,3,5,2,4,6-trioxatriphosphorinane-2,4,6-trioxide; CAS no.: 68957-94-8) as coupling agent.

The reaction proceeds smoothly and furnishes amide-like compound of formula (VI) with high yields. In a one-pot process, carboxylic acid-like compound of formula (VII) (best used with a slight shortage relative to aniline (VIII), ca. 0.90-0.95 equivalents) is placed along with 1.5 equivalents N,N-diisopropylethylamine in 16 volumes THF. Subsequently, 2 equivalents T3P (50 wt % solution in ethyl acetate) are slowly added at 0 to 5° C. The reaction mixture is additionally stirred for 2 to 4 h, preferably 2 h at 0 to 5° C.

The mixture was then quenched with water, its pH adjusted with sodium carbonate aq. solution to app. 7.4 and the THF/ethyl acetate mixture was largely distilled off (200 mbar, 45-50° C. internal temperature). Subsequently, water and ethanol were added and the pH was adjusted to app. 7.0 by adding sodium carbonate aq. solution. The mixture was stirred 1 to 5 h, preferably 1 to 2 h, at 50° C., then cooled to 20 to 25° C. and stirred for 10 to 30 min. The product was isolated via filtration and subsequently washed with a mixture of ethanol and water and finally dried under vacuum at 45° C. With this process, typically very high yields between 95 to 96% were obtained. The purity was in all cases >98 area % (HPLC).

In some cases, especially when aniline-like compound of formula (VIII) of poor optical quality (e.g. dark brown color) was used as starting material, it proved useful to perform a treatment with activated charcoal. This procedure is described in the following section:

Crude amide (VI) was dissolved in a mixture of methanol and THF (2:1) and activated charcoal was added. The mixture was heated to 60 to 65° C. for 1 to 1.5 h. The activated charcoal was filtered off and the filtrate was concentrated (down to 2 volumes relative to input material). Water was added and the product precipitated, was filtered, washed and dried at 55 to 60° C. (under vacuum).

Synthesis of compounds of formulas (VII) and (VIII) have been described in the literature and both are commercially available in large quantities.

For compound according to formula (VII): Cottet, Fabrice; Marull, Marc; Lefebvre, Olivier; Schlosser, Manfred, European Journal of Organic Chemistry, 2003, 8 p. 1559-1568; Carter, Percy H.; Cherney, Robert J.; Batt, Douglas G.; Duncia, John V.; Gardner, Daniel S.; Ko, Soo S.; Srivastava, Anurag S.; Yang, Michael G. Patent: US2005/54627 A1, 2005; Ashimori; Ono; Uchida; Ohtaki; Fukaya; Watanabe; Yokoyama Chemical and Pharmaceutical Bulletin, 1990, vol. 38, 9 p. 2446-2458.

For compound according to formula (VIII): Nissan Chemical Industries, Ltd.; CHUGAI SEIYAKU KABUSHIKI KAISHA, EP2045253 A1, 2009.

Evaluation of the Total Process:

Scheme 2 depicts the total synthesis of pure product of formula (I) from aniline-like compound of formula (VIII). Product of formula (I) is received with a purity of >99 area % (HPLC). When calculating with the best yields achieved for each step, a total yield of 50% is obtained. This also includes the installation of the final crystal form.

Scheme 2: Total synthesis of pure product of formula (I) from the aniline-like compound according to formula (VIII)

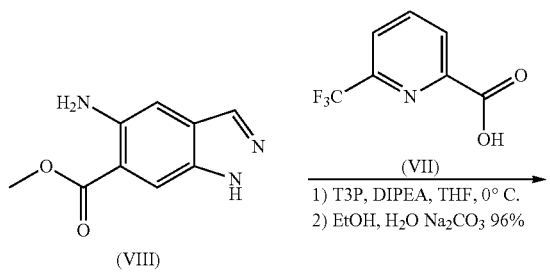

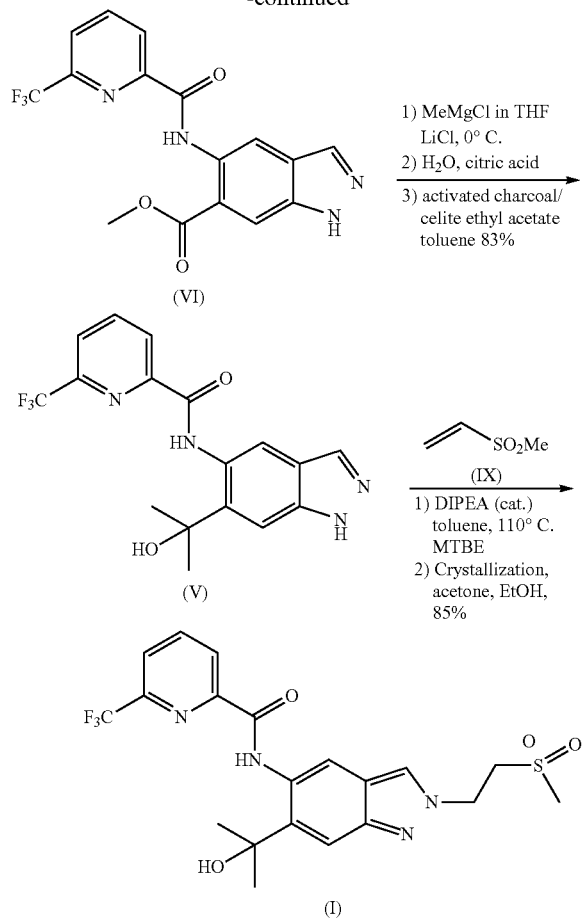

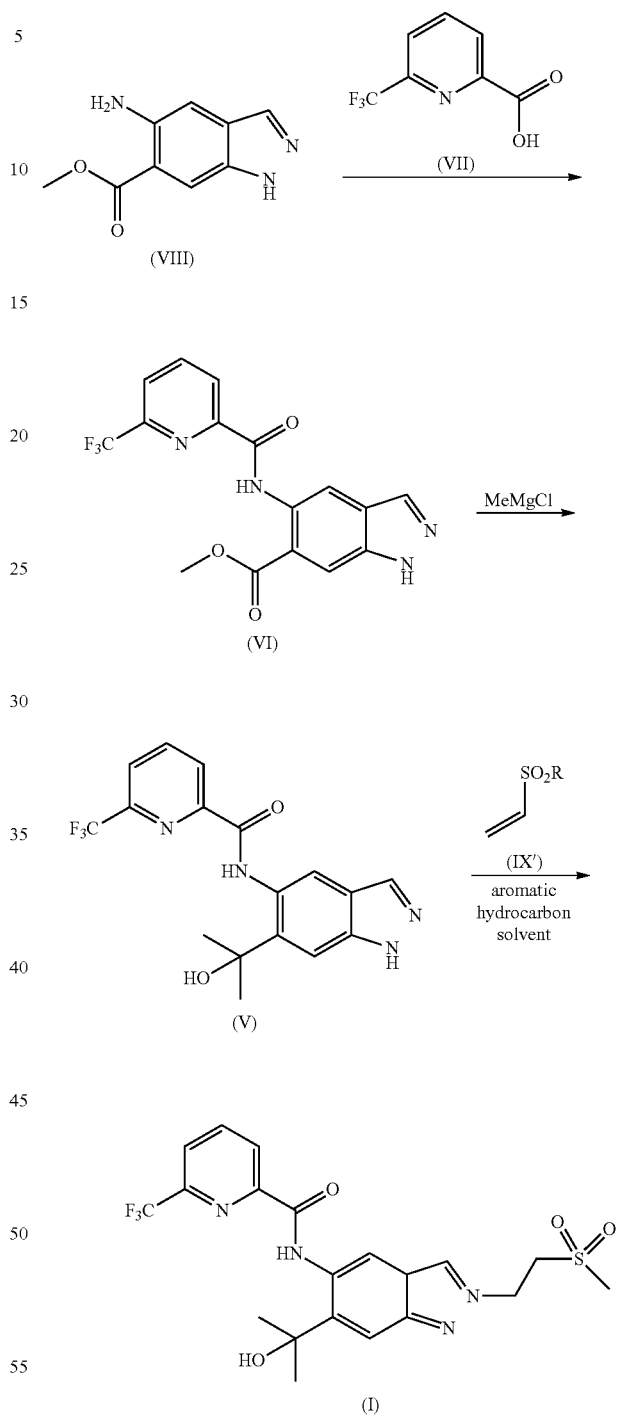

When comparing this total yield with the published prior art data:
1. amide coupling (preparation of compound according to formula (VI)): 84% yield;
2. Grignard reaction followed by chromatographic purification: 45% yield;
3. alkylation with 2-bromoethyl methyl sulfone analogously to methods known in the literature followed by chromatographic purification: 9.68% yield;

the advantages of the new process become very clear:

With the method known from the prior art and as described above, a total yield of only 3.7% could be achieved with the installation of the final crystal form not included.

To conclude, the new inventive process furnishes compound according to formula (I) with a >13 times higher total yield as compared to the prior art. It, moreover, includes the directed and reproducible preparation of the targeted polymorph for production of a pharmaceutical composition, such as a tablet.

It must be emphasized that the reaction of a substituted vinyl sulfone for a directed highly selective preparation of N2-functionalized indazoles is novel, without precedence in the literature and therefore a highly significant invention for the preparation of such substitution patterns.

Hence, in a first aspect, the present invention relates to a method of preparing a compound of formula (I) via the following steps shown in reaction scheme IA, vide infra:

in which R represents an alkyl group, such as a methyl, ethyl or n-propyl group for example, or an aryl group, such as a phenyl group for example, and aromatic hydrocarbon solvent is a solvent such as toluene or xylene for example.

In an embodiment of the first aspect, the present invention relates to a method of preparing a compound of formula (I) via the following steps shown in reaction scheme I, vide infra:

Scheme I: Preparation of compound of formula (I) from compound of formula (VIII) as starting material

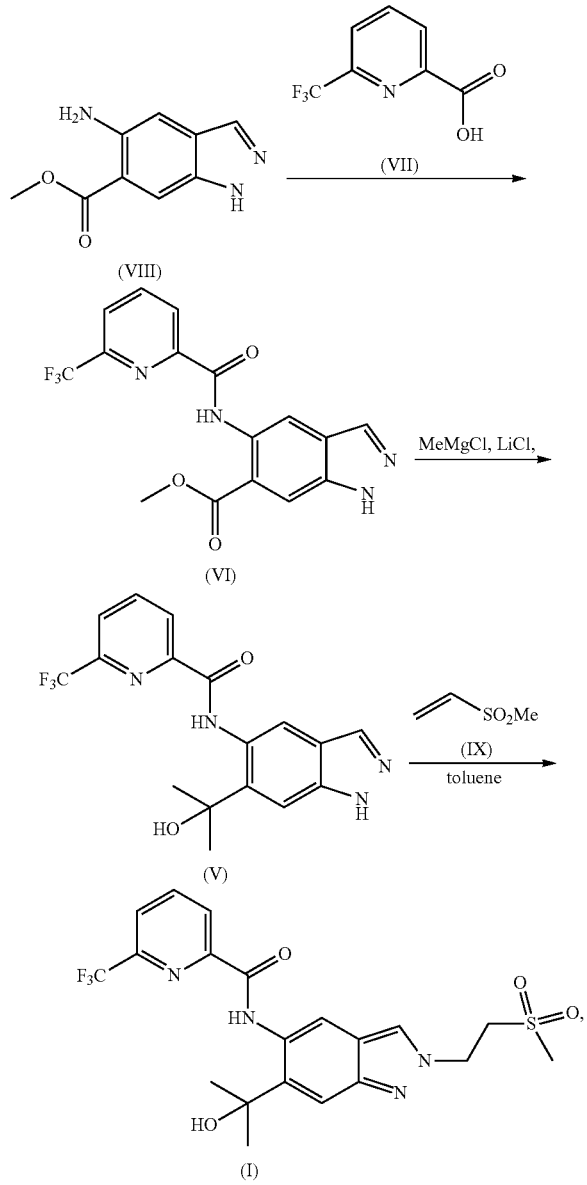

In an embodiment of the first aspect, the present invention relates to a method of preparing a compound of formula (I):

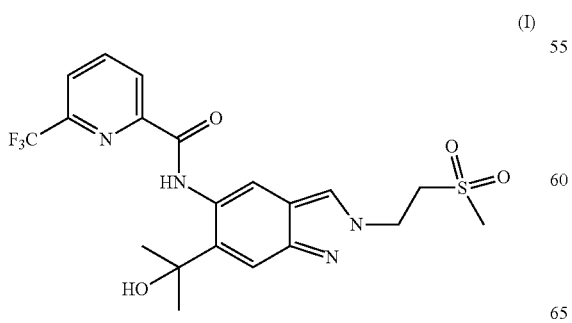

comprising the following step (A):
wherein a compound of formula (V):

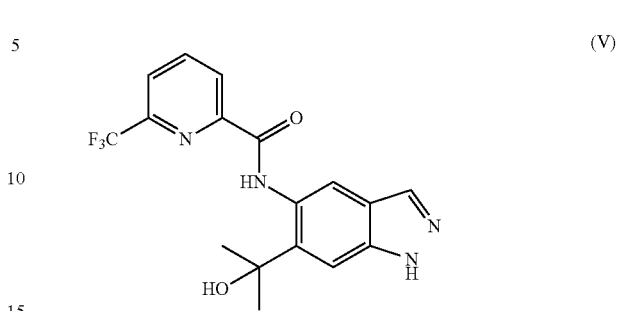

is allowed to react with a vinyl sulfone compound of formula (IX'):

in which R represents an alkyl group, such as a methyl, ethyl or n-propyl group for example, or an aryl group, such as a phenyl group for example,
optionally in an aromatic hydrocarbon solvent, such as toluene or xylene for example, preferably at the reflux temperature of said solvent,
thereby providing said compound of formula (I).

In an embodiment of the first aspect, the present invention relates to a method of preparing a compound of formula (I) as described supra, wherein said aromatic hydrocarbon solvent is toluene.

In an embodiment of the first aspect, the present invention relates to a method of preparing a compound of formula (I) as described supra, wherein said compound of formula (V):

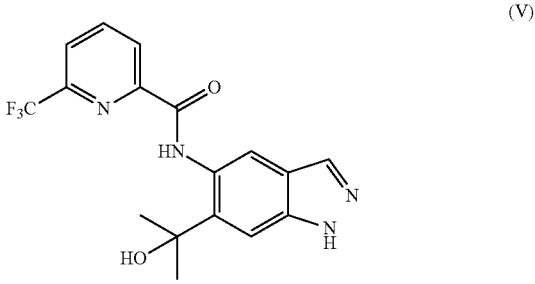 [SMILES: CC(C)(O)c1cc2[nH]ncc2cc1NC(=O)c1cccc(C(F)(F)F)n1]

is prepared by the following step (B):
wherein a compound of formula (VI):

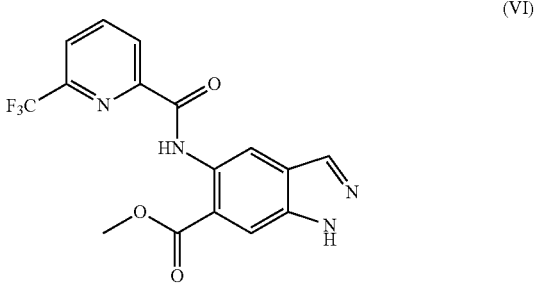 [SMILES: COC(=O)c1cc2[nH]ncc2cc1NC(=O)c1cccc(C(F)(F)F)n1]

is allowed to react with a reductive methylating agent, such as a methylmetallic agent, such as a methylmagnesium halide, such as methylmagnesium chloride for example, optionally in the presence of an alkali metal halide, such as lithium chloride for example, thereby providing said compound of formula (V).

In an embodiment of the first aspect, the present invention relates to a method of preparing a compound of formula (I) as described supra, wherein said compound of formula (VI):

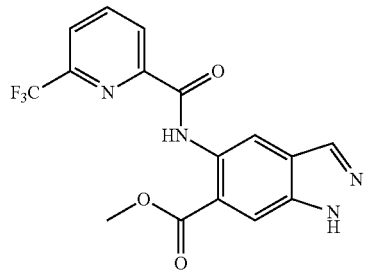

(VI)

is prepared by the following step (C):
wherein a compound of formula (VIII):

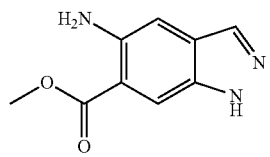

(VIII)

is allowed to react with a compound of formula (VII):

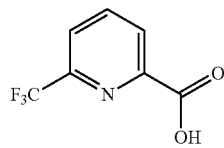

(VII)

optionally in the presence of an organic base, particularly a weak organic base, such as a tertiary amine, such as N,N-diisopropylethylamine for example, optionally in the presence of a coupling agent, such as 2,4,6-tripropyl-1,3,5,2,4,6-trioxatriphosphinane 2,4,6-trioxide (T3P) for example, thereby providing said compound of formula (VI).

In a further embodiment of the first aspect, the present invention relates to a method of preparing a compound of formula (I) as described supra, wherein said compound of formula (I) is purified by crystallization, particularly from a solvent such as ethanol or isopropanol, for example.

In a variant of said further embodiment of the first aspect, said solvent is ethanol.

In a variant of said further embodiment of the first aspect, said solvent is isopropanol.

In an embodiment of the first aspect, the present invention relates to a method of preparing a compound of formula (I) as described supra, wherein said compound of formula (I) is in the form of polymorph (B).

In accordance with a second aspect, the present invention relates to polymorph (B) of the compound of formula (I):

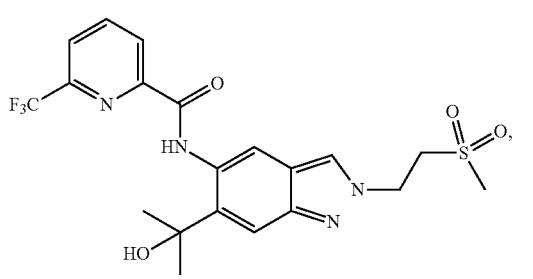

(I)

as prepared by the method as described supra.

In accordance with a third aspect, the present invention relates to polymorph (B) of the compound of formula (I):

(I)

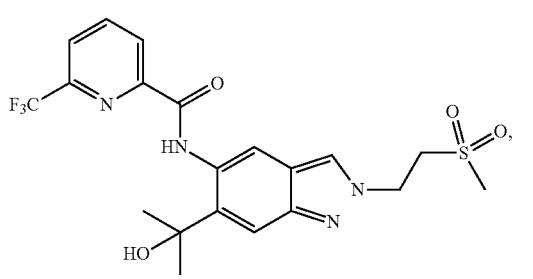

In accordance with an embodiment of the third aspect, the present invention relates to said polymorph (B) as described supra, having an XRPD peak maxima [° 2 Theta] (Copper (Cu)) as follows:

TABLE 2

| XRPD of polymorph B of compound (I) Reflections [Peak maximum °2Theta] Polymorph B |
|---|
| 4.4 |
| 8.9 |
| 9.3 |
| 9.7 |
| 10.1 |
| 12.4 |
| 12.9 |
| 13.3 |
| 14.1 |
| 14.7 |
| 15.4 |
| 16.1 |
| 16.4 |
| 16.7 |
| 17.3 |
| 17.9 |
| 18.3 |
| 18.4 |
| 18.5 |
| 19.2 |
| 19.4 |
| 19.7 |
| 20.2 |
| 20.6 |
| 21.2 |
| 21.4 |

TABLE 2-continued

XRPD of polymorph B of compound (I)
Reflections [Peak maximum °2Theta]
Polymorph B 21.9
22.3
22.6
22.8
23.6
24.5
24.9
25.2
25.5
25.8
27.2
27.5
28.8
29.6
30.2
31.2
31.5
32.5
33.5
33.9
35.1
36.2
37.6

BRIEF DESCRIPTION OF THE DRAWINGS

FIG. 1 shows the X-Ray powder diffractogram (at 25° C. and with Cu—K alpha 1 as radiation source) of the compound of formula (I) in the polymorphic form B.

In accordance with a fourth aspect, the present invention relates to the use of a compound selected from:

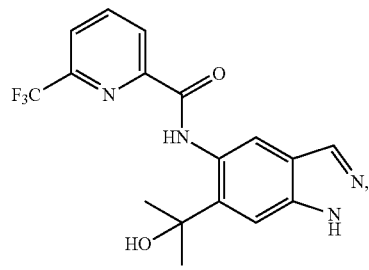

(V)

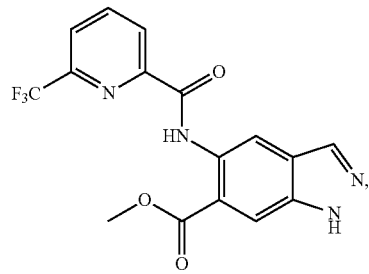

(VI)

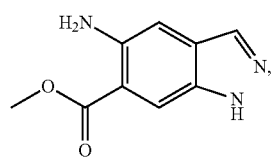

(VIII)

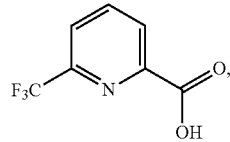

(VII)

for preparing a compound of formula (I):

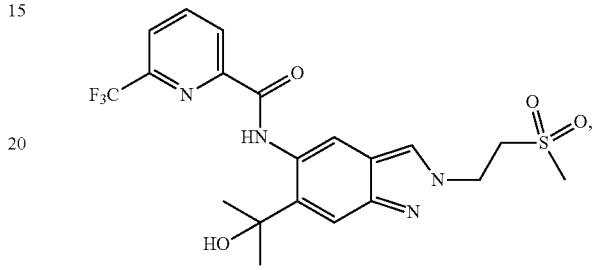

(I)

or polymorph B of the compound of formula (I) as described supra, by the method as described supra.

In accordance with a fifth aspect, the present invention relates to the use of a vinyl sulfone compound of formula (IX'):

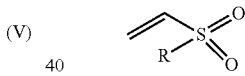

(IX')

in which R represents an alkyl group, such as a methyl, ethyl or n-propyl group for example, or an aryl group, such as a phenyl group for example, for preparing a compound of formula (I):

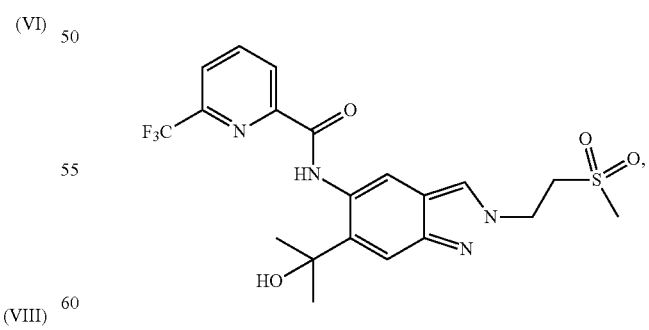

(I)

or polymorph B of the compound of formula (I) as described supra.

In an embodiment of the fifth aspect, the present invention relates to use wherein said vinyl compound of formula (IX') is methyl vinyl sulfone.

Methods

HPLC
Method A
Device: Agilent Technologie 1260 Infinity with 1290 Infinity Sampler & Agilent 1100 Series
Zorbax SB-AQ, 50*4.6 mm, 1.5 μm Buffer: Ammonium dihydrogen phosphate pH: 2.4
Acetonitrile
0 min. 5% buffer
8.3 min 80% buffer
11 min. 80% buffer
210 nm/4 nm
1.2 ml/min.

|  | Method B |  |
|---|---|---|
| Apparatus | 1. Agilent Technologies, HPLC 1290 Infinity (with DAD): Ultra-High performance liquid chromatograph thermostatically controlled column oven, UV-detector and data evaluation system<br>2. Stainless steel column<br>  Length: 5 cm<br>  Internal diameter: 2.1 mm<br>  Filling: SB-Aq Rapid Resolution HD, 1.8 μm |  |
| Reagents | 1. Acetonitrile, for the HPLC<br>2. Tetrahydrofuran, for the HPLC<br>3. Water, analytical grade<br>3. Phosphoric acid 85%, analytical grade |  |
| Test solution | Dissolve the sample compound of formula (I) in a tetrahydrofuran in a concentration of 0.5 mg/ml. (e.g. dissolve approx. 25 mg sample compound of formula (I), accurately weighed in acetonitrile 50 ml) |  |
| Calibration solution | Dissolve the reference standard compound* in acetonitrile in a concentration of 0.5 mg/ml (e.g. dissolve approx. 25 mg reference standard, accurately weighed, in acetonitrile 50 ml).<br>* reference standard compound means the compound, which has to be analyzed, as highly pure compound, i.e. >97 area % HPLC |  |
| Control solution | Prepare a control solution that is identical with the calibration solution. Additionally, the control solution contains small amounts of the organic impurities. |  |
| Detection sensitivity solution | Prepare a solution containing the component Solbrol P (CAS-no.: 94-13-3; propyl 4-hydroxybenzoate) (RT approx. 2.80 min) diluted to a concentration of 0.76 μg/ml. |  |
| HPLC conditions | The above described conditions are for example. To achieve optimal separations, they should, if necessary, be adapted to the technical possibilities of the chromatograph and the properties of the respective column. |  |
| Eluent | A. water:tetrahydrofuran (v:v) 9:1, then add 0.1% phosphoric acid 85%<br>B. Acetonitrile:tetrahydrofuran 9:1 |  |
| Flow rate | 0.8 mL/min |  |
| Temperature of the column oven | 40° C. |  |
| Temperature of the sample chamber | room temperature |  |
| Detection | Measuring wavelength: 220 nm<br>Bandwidth: 6 nm |  |
| Injection volume | 2.0 μL |  |
| Draw Speed | 200 μL/min |  |
| Needle Wash | Solvent for flush port:tetrahydrofuran |  |
| Datenrate | 10 Hz |  |
| Cell Dimension | 10 mm |  |
| Equilibration time | 10 min (at starting conditions) |  |
| Gradient | Time [min] | % A | % B |
|  | 0 | 95 | 5 |
|  | 1 | 85 | 15 |
|  | 4 | 80 | 20 |
|  | 6 | 40 | 60 |
|  | 8 | 20 | 80 |
|  | 12 | 20 | 80 |
| Runtime of the chromatogram | 12 min |  |
| Calculation of assay (content) | The assay is calculated using linear regression and taking into account the sample weight, assay and weight of the reference standard, with a validated chromatographic data system (e.g. Empower). |  |

GC-HS

Residual solvent analysis via headspace gas chromatography (GC-HS)

Agilent 6890 gas chromatograph with split-injection and FID (column: Restek Rxi Sil MS; length: 20 m; internal diameter: 0.18 mm; $d_f$=1 μm). Injector temp 160° C., flow 1.2 ml/min ($H_2$) Split Ratio 18, oven Temp 40° C. (4.5 min)-14° C./min-70° C.-90° C./min-220° C. (1.69 min). Detector: temp 300° C., 400 ml/min (synth air), 40 ml/min ($H_2$), 30 ml/min ($N_2$), rate 20 Hz.

Perkin Elmer Turbomatrix 40 headspace sampler: oven 80° C., needle 150° C., transfer line 160° C., system pressure 140 kPa, equilibration time 32 min, pressurization 4.0 min, injection time 0.04 min (Sampler) 0.05 min (GC).

Sample concentration: 20 mg substance in 2 ml DMF

X-Ray Crystallography: Measurement Conditions:

| | |
|---|---|
| Anode material | Cu |
| K-Alpha1 [Å] | 1.54060 |
| Generator settings | 40 mA, 40 kV |
| Primary beam monochromator | focussing X-ray mirror |
| Rotated sample | Yes |
| Scan axis | Gonio |
| Start Position [°2Th.] | 2.0066 |
| End Position [°2Th.] | 37.9906 |

WORKING EXAMPLES

The following examples illustrate the present invention.

Preparation of N-{6-(2-Hydroxypropan-2-yl)-2-[2-(methylsulphonyl)ethyl]-2H-indazol-5-yl}-6-(trifluoromethyl)pyridine-2-carboxamide (I)

Example #1

Methyl 5-({[6-(trifluoromethyl)pyridin-2-yl]carbonyl}amino)-1H-indazole-6-carboxylate (VI)

2000 g (10.46 mol) methyl 5-amino-1H-indazole-6-carboxylate, 1899 g (9.94 mol) 6-(trifluoromethyl)pyridine-2-carboxylic acid and 2028 g (15.69 mol) N,N-diisopropylethylamine are mixed in 14.2 kg THF. At 0 to 5° C., 13.3 kg of a solution of T3P in ethyl acetate (50 wt %) is added dropwise within 30 min. Stirring is continued for 2 h at the same temperature.

Work-Up:

The reaction mixture is warmed to ambient temperature (20° C.). 3000 g of water are added while the temperature is kept at 20 to 25° C. Stirring is continued for 10 min. The pH is adjusted to ca. 7.4 (7-8) using 4 N aq. sodium carbonate solution. Stirring is continued for 10 min. If necessary the pH is again adjusted to 7.4 using 4 N aq. sodium carbonate solution.

The solvents (THF/ethyl acetate) are evaporated under reduced pressure (appr. 200 mbar, 45-50° C. internal temperature) until the limit of stirring is reached. A mixture of 4.7 kg ethanol and 14.0 kg water is added and the pH is again adjusted to pH 7.4 (7-8) using 4 N aq. sodium carbonate solution.

The mixture is stirred for 1 h at 50° C., subsequently cooled to 20 to 25° C. Stirring is continued for 10 min at the same temperature. The precipitated crystals are filtered, washed with a mixture of ethanol and water (1.3 kg ethanol with 4 kg water) and dried under vacuum in a drying oven (45° C., $N_2$ flux, at least 12 h).

According to the above described procedure four batches using 2 kg of starting material (methyl 5-amino-1H-indazole-6-carboxylate) were produced in the technical laboratory:

Yields:
Batch #1: 3476 g (95%)
Batch #2: 3449 g (95%)
Batch #3: 3476 g (95%)
Batch #4: 3494 g (96%)

The purities of all batches were determined to be >98 area % (HPLC).

HPLC (Method A): Rt=6.5 min.

MS (ESI pos): m/z=365 (M+H)$^+$ $^1$H NMR (500 MHz, DMSO-d6): δ [ppm]: 3.98 (s, 3 H), 8.21 (d, 1H), 8.25 (s, 1H), 8.31 (s, 1H), 8.39 (t, 1H), 8.48 (d, 1H), 9.16 (s, 1H), 12.57 (s, 1H), 13.45 (br s, 1H).

$^1$H NMR (300 MHz, DMSO-d6): δ [ppm]=3.97 (s, 3 H), 8.13-8.27 (m, 2 H), 8.30 (s, 1 H), 8.33-8.45 (m, 1 H), 8.45-8.51 (m, 1 H), 9.15 (s, 1 H), 12.57 (s, 1 H), 13.44 (br s, 1 H).

Example #2

N-[6-(2-hydroxypropan-2-yl)-1H-indazol-5-yl]-6-(trifluoromethyl)pyridine-2-carboxamide (V)

In the following section, different variants of the reaction procedure and work-up are described. These procedures are oriented at the given conditions in the respective technical plants.

The following experiments were performed at the exclusion of water and air using inert gas (N2 or Ar).

Variant #1

50 g (137.255 mmol) of methyl 5-({[6-(trifluoromethyl)pyridin-2-yl]carbonyl}amino)-1H-indazole-6-carboxylate (VI) were dissolved in 800 ml THF. Under normal pressure (1 atm) ca. 300 ml THF were distilled off at 70° C. The solution was then cooled to 0 to 3° C.

The solution was kept at this temperature and added dropwise within 120 min to a cooled mixture of 457.5 ml (1372.6 mmol) methylmagnesium chloride 3 M in THF and 29.1 g lithium chloride (686.3 mmol) at 0 to 3° C. After the addition was completed, a sample was taken out of the mixture and subjected to HPLC analysis showing that conversion was completely done. The mixture was poured carefully over 25 min at 0 to 3° C. into 500 ml ½-sat. aq. sodium chloride solution (attention: exothermic! During the first 50 ml a strong rise in temperature to 29° C. was observed!). A suspension was received which dissolved when 358 ml 20 wt % aq. citric acid were added (pH dropped from 8.08 to 4.28). Stirring was continued for 10 min at 20 to 25° C. 500 ml of ethyl acetate were added and stirring was continued for 10 min. The phases were separated. The mulm was added to the organic phase. 5 g of activated charcoal were added to the organic phase. The mixture was heated to 78° C. (internal temperature), stirred for 30 min at that temperature and subsequently cooled to 50° C. (internal temperature). The warm solution was filtered over celite and washed twice with 125 ml ethyl acetate. The mixture was concentrated to ca. 150 ml at ambient pressure (1 atm) and 110° C. 350 ml of toluene were added and 200 ml were distilled off at ambient pressure (1 atm) and 110° C. The product precipitated. At 60° C. internal temperature, 200 ml n-heptane were added over 45 min. The mixture was cooled to 0 to 3° C. and stirred for 2 h at this temperature. The product was filtered and washed twice with a mixture of 50 ml toluene/n-heptane (1:1). The precipitated product was dried in a drying oven at 40° C. and 20 mbar for >48 h.

Yield: 39.42 g (78.83%, purity 97.84 area % HPLC)
HPLC (Method A): Rt=5.8 min.
MS (ESIpos): m/z=365 (M+H)$^+$
$^1$H-NMR (400 MHz, DMSO-d6): δ [ppm]=1.63 (s, 6H), 5.99 (s, 1H), 7.50 (s, 1H), 8.06 (s, 1H), 8.17 (d, 1H), 8.37 (t, 1H), 8.46 (d, 1H), 8.78 (s, 1H), 12.33 (s, 1H), 12.97 (br s, 1H).

13 batches were produced following the procedure of variant #1. The table 3 below summarizes the respective yields. The reactions were performed at 1 kg scale with regard to the use of methyl 5-({[6-(trifluoromethyl)pyridin-2-yl]carbonyl}amino)-1H-indazole-6-carboxylate (VI) as starting material. In most cases, two of batches were united after treatment with activated charcoal:

TABLE 3

Yields obtained for batches 1 to 13 of synthesis of (V) from (VI)

| Batch # | Yield [kg] [%] |
|---|---|
| 1 | 1.60 kg |
| 2 | 79.9% |
| 3 | 1.88 kg |
| 4 | 94.0% |
| 5 | 1.82 kg |
| 6 | 90.8% |
| 7 | 1.66 kg |
| 8 | 83.0% |
| 9 | 1.75 kg |
| 10 | 87.6% |
| 11 | 1.85 kg |
| 12 | 92.7% |
| 13* | 0.92 kg |
|  | 96.4% |

*single batch

Variant #2

30 g (82.4 mmol) methyl 5-({[6-(trifluoromethyl)pyridin-2-yl]carbonyl}amino)-1H-indazole-6-carboxylate (VI) were dissolved in 480 ml THF. Under normal pressure (1 atm) ca. 180 ml THF were distilled off at 70° C. The mixture (slight suspension) was then cooled to 0 to 3° C.

The solution was kept at this temperature and added dropwise within 120 min to a cooled mixture of 274.5 ml (823.5 mmol) methylmagnesium chloride 3 M in THF and 17.5 g lithium chloride (411.8 mmol) at 0 to 3° C. 15 min after the addition was completed, a sample was taken out of the mixture and subjected to HPLC analysis showing that (VI) was completely converted. The mixture was poured carefully over 15 min at 0 to 3° C. into 300 ml of water (attention: exothermic! During the first 50 ml a strong rise in temperature was observed!). 310 ml 20 wt % aq. citric acid were added (pH dropped to 4.05). Stirring was continued for 60 min at 20 to 25° C. 300 ml of ethyl acetate were added and stirring was continued for 30 min. The phases were separated. The mulm was added to the organic phase. The organic phase was washed twice with 450 ml of water. The organic phase was concentrated to 350 ml at 65° C. (internal temperature) and ambient pressure (1 atm). 250 ml ethyl acetate were added. 6 g of activated charcoal were added to the organic phase. The mixture was heated to 65° C. (internal temperature), stirred for 120 min at that temperature and subsequently cooled to 50° C. (internal temperature). The warm solution was filtered over celite and washed twice with 125 ml ethyl acetate. The mixture was concentrated to ca. 150 ml at ambient pressure (1 atm) and 110° C. 300 ml of toluene were added and 200 ml were distilled off at ambient pressure (1 atm) and 110° C. The product precipitated. At 60° C. internal temperature, 200 ml n-heptane were added over 45 min. The mixture was cooled to 0-3° C. and stirred for 2 h at this temperature. The product was filtered and washed twice with a mixture of 50 ml toluene/n-heptane (1:1). The precipitated product was dried in a drying oven at 40° C. and 20 mbar for >48 h.

Yield: 24.0 g (80%, purity: 95.8 area % HPLC)
HPLC (Method A): Rt=5.8 min.
MS (ESI pos): m/z=365 (M+H)$^+$
$^1$H-NMR (400 MHz, DMSO-d6): δ [ppm]=1.63 (s, 6H), 5.99 (s, 1H), 7.50 (s, 1H), 8.06 (s, 1H), 8.17 (d, 1H), 8.37 (t, 1H), 8.46 (d, 1H), 8.78 (s, 1H), 12.33 (s, 1H), 12.97 (br s, 1H).

Variant #3

30 g (82.4 mmol) methyl 5-({[6-(trifluoromethyl)pyridin-2-yl]carbonyl}amino)-1H-indazole-6-carboxylate (VI) were dissolved in 600 ml THF. Under normal pressure (1 atm) ca. 150 ml THF were distilled off at 70° C. The mixture (slight suspension) was then cooled to 0-3° C.

The solution was kept at this temperature and added dropwise within 120 min to a cooled mixture of 274.5 ml (823.5 mmol) methylmagnesium chloride 3 M in THF and 17.5 g (411.8 mmol) lithium chloride at 0-3° C. The dropping funnel was rinsed twice with 10 ml THF. 15 min after the addition was complete, a sample was taken out of the mixture and subjected to HPLC analysis showing that (VI) was completely converted. The mixture was poured carefully over 10 min at 0-3° C. into 300 ml of water (attention: exothermic! During the first 50 ml a strong rise in temperature to 25° C. was observed!). 250 ml 20 wt % aq. citric acid were added (pH dropped from 8 to 4). Stirring was continued for 30 min at 20-25° C. 300 ml of ethyl acetate were added and stirring was continued for 10 min. The phases were separated. The mulm was added to the organic phase. The organic phase was washed twice with 200 ml of 1 wt % sodium chloride aq. solution. The phases were separated. The organic phase was concentrated to 250 ml at 65° C. (internal temperature) and ambient pressure (1 atm). 150 ml ethyl acetate and 6 g of activated charcoal were added to the organic phase. The mixture was heated to 65° C. (internal temperature), stirred for 120 min at that temperature and subsequently cooled to 50° C. (internal temperature). The warm solution was filtered over celite and washed twice with 50 ml ethyl acetate. The mixture was concentrated to ca. 100 ml at ambient pressure (1 atm) and 110° C. 300 ml of isopropanol were added. 300 ml were distilled off at ambient pressure (1 atm) and 110° C. 300 ml isopropanol were added again and distilled off (ca. 355 ml) at 110° C. The resulting suspension was cooled to 20-25° C. 45 ml water were added over 45 min. The mixture was stirred for 1 h. The precipitated product was filtered and washed with 50 ml of a water/isopropanol (1:1) mixture. The precipitated product was dried in a drying oven at 50° C. and 20 mbar for >48 h.

Yield: 24.9 g (83%, purity: 97.84 area % HPLC)
HPLC (Method A): Rt=5.8 min.
MS (ESI pos): m/z=365 (M+H)$^+$
$^1$H-NMR (400 MHz, DMSO-d6): δ [ppm]=1.63 (s, 6H), 5.99 (s, 1H), 7.50 (s, 1H), 8.06 (s, 1H), 8.17 (d, 1H), 8.37 (t, 1H), 8.46 (d, 1H), 8.78 (s, 1H), 12.33 (s, 1H), 12.97 (br s, 1H).

Variant #4

This variant was used for the production of technical batches at kg scale (>10 kg) (see table 4).

60 g (164.7 mmol) methyl 5-({[6-(trifluoromethyl)pyridin-2-yl]carbonyl}amino)-1H-indazole-6-carboxylate (VI) were dissolved in 1500 ml THF. Under normal pressure (1 atm) ca. 600 ml THF were distilled off at 70° C. The mixture (yellow solution) was then cooled to 0-3° C.

The solution was kept at this temperature and added dropwise within 120 min to a cooled mixture of 550 ml (1647.1 mmol) methylmagnesium chloride 3 M in THF and 35 g (823.5 mmol) lithium chloride at 0-3° C. 15 min after the addition was complete, a sample was taken out of the mixture and subjected to HPLC analysis showing that (VI) was completely converted. The mixture was poured carefully over 15 min at 0-3° C. into 600 ml of water (attention: exothermic! During the first 50 ml a strong rise in temperature was observed!). 600 ml 20 wt % aq. citric acid were added (pH dropped to 4). Stirring was continued for 30 min at 20-25° C. The phases were separated. The organic phase was washed twice with 400 ml of 1 wt % sodium chloride aq. solution. The mulm was added to the organic phase. The phases were separated. The organic phase was concentrated to 700 ml at 65° C. (internal temperature) and ambient pressure (1 atm). 500 ml ethyl acetate and 12 g of activated charcoal were added to the organic phase. The mixture was heated to 65° C. (internal temperature), stirred for 120 min at that temperature and subsequently cooled to 50° C. (internal temperature). The warm solution was filtered over celite and washed twice with 200 ml ethyl acetate. Concentration was continued under reduced pressure (200 mbar). A solvent swap to toluene was performed (remaining volume ca. 850 mL). The resulting suspension was cooled to 0-3° C. The precipitated product was filtered and washed with 50 ml of toluene. The precipitated product was dried in a drying oven at 50° C. and 20 mbar for >48 h.

Yield: 51.2 g (85.3%, purity 96.51 area % HPLC)
HPLC (Method A): Rt=5.8 min.
MS (ESI pos): m/z=365 (M+H)$^+$
$^1$H-NMR (400 MHz, DMSO-d6): δ [ppm]=1.63 (s, 6H), 5.99 (s, 1H), 7.50 (s, 1H), 8.06 (s, 1H), 8.17 (d, 1H), 8.37 (t, 1H), 8.46 (d, 1H), 8.78 (s, 1H), 12.33 (s, 1H), 12.97 (br s, 1H).

Variant #5
Purification Via Stirring in Isopropanol/Water

Depending on the purity of the crude product, an additional purification step via stirring in mixtures of isopropanol and water, preferably 1:1, can be performed. Depending on the purity of the crude product, stirring is performed in a range of 2-10 volumes with regard to the crude starting material. The following example describes stirring in 3 volumes isopropanol/water:

7.5 g N-[6-(2-hydroxypropan-2-yl)-1H-indazol-5-yl]-6-(trifluoromethyl)pyridine-2-carboxamide (V) with a purity of 95 area % (HPLC) are stirred in 22.5 ml of a 1:1 (vol) mixture of water and isopropanol for 2 h at 20° C. The suspension was then filtered and the product washed with 4 ml of the same solvent mixture. The product was dried in drying oven at 50° C. under vacuum (<100 mbar).

Yield: 6.8 g (90.7%, purity >98 area % HPLC)
HPLC (Method A): Rt=5.8 min.
MS (ESIpos): m/z=365 (M+H)$^+$
$^1$H-NMR (400 MHz, DMSO-4): δ [ppm]=1.63 (s, 6H), 5.99 (s, 1H), 7.50 (s, 1H), 8.06 (s, 1H), 8.17 (d, 1H), 8.37 (t, 1H), 8.46 (d, 1H), 8.78 (s, 1H), 12.33 (s, 1H), 12.97 (br s, 1H).

A combination of variant #4 and #5 was performed at 44 kg scale (see table 4 below).

TABLE 4

Manufacturing of compound according to formula (V) following the protocols of variant #4 and #5

| Batch # | Yield | Content (Assay for use) |
|---|---|---|
| 1 | 38.4 kg 79% | 95.9% |
| 2 | 33.6 kg 76% | 96.0% |

Example #3

N-{6-(2-Hydroxypropan-2-yl)-2-[2-(methylsulphonyl)ethyl]-2H-indazol-5-yl}-6-(trifluoromethyl)pyridine-2-carboxamide (I)

Variant #1

This variant was used for the production of technical batches at kg scale and follows the protocol described in WO2016/083433.

2.5 kg (6.86 mol) N-[6-(2-hydroxypropan-2-yl)-1H-indazol-5-yl]-6-(trifluoromethyl)pyridine-2-carboxamide (V) were suspended in 33 l (28.6 kg) toluene. The mixture was heated to reflux and app. 8 l toluene were distilled off the mixture. The mixture was cooled to 90° C. and 44 g (0.34 mol) of N,N-diisopropylethylamine were dosed to the mixture. The mixture was stirred for further 15 min at 90° C. before 1.17 kg (10.98 mmol) methyl vinyl sulfone were added. The reaction mixture was kept at 112° C. (reflux toluene) and stirred for at least 72 h. The mixture was cooled to 20° C. The mixture was then heated to reflux and 8 l of toluene were distilled off the mixture. The mixture was then cooled to 70° C. and 12.6 kg methyl tert-butyl ether (MTBE) were added within 30 min. The mixture was cooled to 20° C. within 2 h and stirred at 20° C. overnight. It was then cooled to 0° C. and stirred for 1 h. The precipitate was filtered off and washed twice with 3 l of cold MTBE. The crystalline product was dried in an oven at 50° C. under vacuum.

Yield: 2.39 kg (73.9%, purity: 97.8 area % HPLC)
HPLC (Method B): Rt=3.07 min.
MS (ESIpos): m/z=471 (M+H)$^+$
$^1$H NMR (400 MHz, DMSO-d$_6$): δ [ppm]=1.63 (s, 6 H), 2.90 (s, 3 H), 3.85 (t, 2 H), 4.86 (t, 2 H), 5.97 (s, 1 H), 7.59 (s, 1 H), 8.13-8.19 (m, 1 H), 8.37 (s, 1 H), 8.41-8.48 (m, 2 H), 8.74 (s, 1 H), 12.37 (s, 1 H).

TABLE 5

Yields and purity (in % after HPLC) obtained for three batches of (I) from (V)

| Starting Material (V) Amount [kg] | Product (I) Yield [kg], [%] | Product (I) Purity [area %] (HPLC)* |
|---|---|---|
| 2.50 | 2.47, 76.5 | 97.4 |
| 2.50 | 2.32, 71.4 | 97.2 |
| 2.50 | 2.39, 73.9 (described) | 97.8 (described) |

*Method B

For obtaining material with very high purity and with a defined crystalline form (polymorph B), an additional purification step was introduced.

1.85 kg of crude N-{6-(2-hydroxypropan-2-yl)-2-[2-(methylsulphonyl)ethyl]-2H-indazol-5-yl}-6-(trifluoromethyl)pyridine-2-carboxamide (I) were dissolved in 36.6 kg (46.3 l) of acetone at ambient temperature. The resulting solution was dosed into refluxing ethanol during 2.5 h. During the dosing process 54 l of solvent were distilled off and an internal temperature of 63° C. was reached. Additional 20.8 l ethanol were added and 27 l of solvents were distilled off the mixture. Additionally, 10.2 l additional ethanol were added and 9.3 l were distilled off the mixture. Finally, another 10.2 l additional ethanol were added and 10.2 l of solvents were distilled off the mixture. The mixture was cooled to 20° C. within 3 h and stirred overnight. The mixture was cooled to 0-2° C. within 1.5 h and stirred at this temperature for additional 3 h. The suspension was filtered and the precipitate was washed with 2×0.93 l cold ethanol. The product was dried in a drying oven at 50° C. under vacuum.

Yield: 1.59 kg (85.7%, purity: 99.0 area % HPLC)
HPLC (Method B): Rt=3.07 min.
MS (ESI pos): m/z=471 (M+H)$^+$
$^1$H NMR (400 MHz, DMSO-d$_6$): δ [ppm]=1.63 (s, 6 H), 2.90 (s, 3 H), 3.85 (t, 2 H), 4.86 (t, 2 H), 5.97 (s, 1 H), 7.59 (s, 1 H), 8.16 (d, 1 H), 8.37 (t, 1 H), 8.41-8.48 (m, 2 H), 8.74 (s, 1 H), 12.37 (s, 1 H).

TABLE 6

Yield and purity obtained from synthesis as well as purity (%) after HPLC for (I) synthesized from (V)

| Starting Material: Crude (I) Amount [kg], Purity [area %] (HPLC) | Product (I) Yield [kg], [%] | Product (I) Purity [area %] (HPLC)* |
|---|---|---|
| 1.85, 97.4 | 1.56, 84.2 | 98.9 |
| 1.85, 97.2 | 1.59, 86.1 | 99.1 |
| 1.85, 97.8 | 1.59, 85.7 | 99.0 (described) |

Variant #2

This variant was used for the production of technical batches at kg scale.

10 g (27.448 mmol) N-[6-(2-hydroxypropan-2-yl)-1H-indazol-5-yl]-6-(trifluoromethyl)pyridine-2-carboxamide (V) were suspended in 100 ml toluene. 3.496 g (32.937 mmol) methyl vinyl sulfone were added. The reaction mixture was heated to 110° C. (reflux toluene) and stirred for at least 15 h. An additional portion of 583 mg (5.49 mmol) methyl vinyl sulfone was added and the reaction mixture stirred for 7 h at reflux. Further 583 mg (5.49 mmol) methyl vinyl sulfone were added and the reaction mixture stirred for >15 h. According to HPLC analysis, 2.5% of starting material (V) were still in the reaction mixture. The selectivity N1/N2 had amounted to 1:8. 30 ml of toluene were distilled off. The mixture was cooled to 70° C. At this temperature, 70 ml MTBE were dropped within 5 min to the mixture resulting in a suspension. The mixture was cooled to 20° C. overnight. It was then cooled to 0° C. and stirred for 2 h. The precipitate was filtered off and washed twice with 10 ml of cold MTBE. The crystalline product was dried in drying oven for at least 48 h at 50° C. and <100 mbar.

Yield: 8.6 g (66.6%, purity: 94.7 area % HPLC)
HPLC (Method B): Rt=3.07 min.
MS (ESI pos): m/z=471 (M+H)$^+$
$^1$H NMR (400 MHz, DMSO-d$_6$): δ [ppm]=1.63 (s, 6 H), 2.90 (s, 3 H), 3.85 (t, 2 H), 4.86 (t, 2 H), 5.97 (s, 1 H), 7.59 (s, 1 H), 8.16 (d, 1 H), 8.37 (t, 1 H), 8.41-8.48 (m, 2 H), 8.74 (s, 1 H), 12.37 (s, 1 H).

Batches at Technical Scale:

Following the procedure described as variant #2 batches at scales of 3.396 kg and 1.699 kg with regard to starting material (V) were produced:

TABLE 7

Yield for compound (I) synthesized from compound (V)

| Starting Material (V) Amount | Product (I) Yield |
|---|---|
| 3.40 kg | 2.81 kg, 64.1% |
| 1.70 kg | 1.28 kg, 58.2% |

For the production of GMP-grade material and for obtaining a defined crystalline form (polymorph B) for production of a pharmaceutical composition, such as a tablet, an additional purification step was introduced.

1.5 kg of crude N-{6-(2-hydroxypropan-2-yl)-2-[2-(methylsulphonyl)ethyl]-2H-indazol-5-yl}-6-(trifluoromethyl)pyridine-2-carboxamide (I) as obtained from synthesis as described under variant #2 were dissolved in 45 kg of acetone and subjected to clarification filtration (filter cartridge: 3.0 μm→GMP-filtration). The filtrate was concentrated and a solvent swap to ethanol was performed. Thereby, ethanol was added during simultaneous distillation until an internal temperature of 77° C. was reached. The solution was concentrated to 6-7 volumes of ethanol with regard to the starting volume. The mixture was cooled to 20° C. and stirred for 12 h at this temperature. It was then cooled to 0° C. and stirred for additional 3 h. The product was filtered off, and washed twice with 1 kg cold ethanol. The product was dried in a drying oven at 60° C. under vacuum (<100 mbar).

Yield: 1370 g (91.33%). Analogous to the described procedure, three batches were carried out at technical scale, see table 7.

TABLE 8

Yield of pure compound (I) obtained by purification described supra from crude (I)

| Starting Material (crude I) [kg] | Product (pure I) Yield [kg], [%] |
|---|---|
| 1.50 | 1.37 (91.3%) |
| 2.04 | 1.78 (87.5%) |
| 2.03 | 1.86 (91.4%) |

TABLE 9

Analytical data of combined three batches as shown in table 8

| Purity (HPLC)* | ≥99% (area) |
| Content (assay for use) | ≥97.7% (weight) |
| Ethanol | <0.25% (weight)** |
| Pd | <1 ppm |

*Method B;
**GC-HS

The X-ray diffractogram is given in FIG. 1.

The invention claimed is:

1. A method of preparing a compound of formula (I):

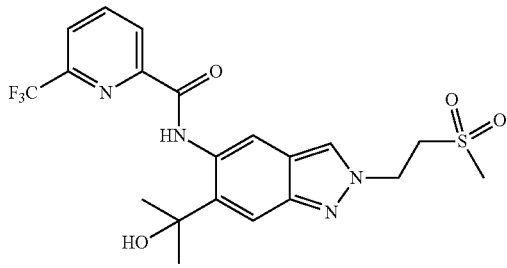 (I)

comprising
reacting a compound of formula (V):

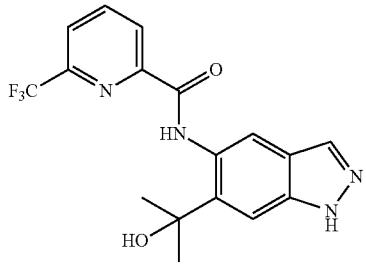 (V)

with a vinyl sulfone compound of formula (IX'):

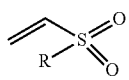 (IX')

wherein R is methyl, to provide the compound of formula (I).

2. The method according to claim 1, wherein the compound of formula (V) is reacted with the compound of formula (IX') in an aromatic hydrocarbon solvent.

3. The method according to claim 1, further comprising reacting a compound of formula (VI):

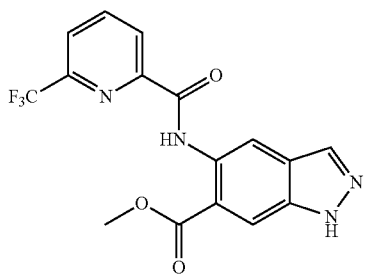 (VI)

with a reductive methylating agent, to provide the compound of formula (V)

4. The method according to claim 3, further comprising reacting a compound of formula (VIII):

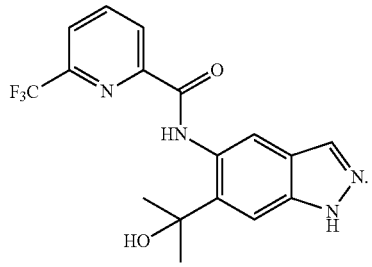 (VIII)

with a compound of formula (VII):

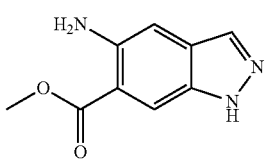 (VII)

to provide the compound of formula (VI)

5. The method according to claim 4,
wherein the compound of formula (V) and the compound of formula (IX') are reacted in an aromatic hydrocarbon solvent, and
wherein the reductive methylating agent is methylmagnesium chloride.

6. The method according to claim 5,
wherein the aromatic hydrocarbon solvent is toluene; and
wherein the compound of formula (VI) is reacted with the reductive methylating agent in the presence of an alkali metal halide wherein the reductive methylating agent is methyl magnesium chloride and the alkali metal halide is lithium chloride.

7. The method according to claim 1, wherein said compound of formula (I) is purified by crystallization.

8. The method according to claim 7, wherein the compound of formula (I) is purified by crystallization from a solvent, and wherein said solvent is ethanol.

9. The method according to claim 7, wherein the compound of formula (I) is purified by crystallization from a solvent, and wherein said solvent is isopropanol.

10. The method according to claim 1, comprising reacting the compound of formula (V) with the compound of formula (IX') in an aromatic hydrocarbon solvent at the reflux temperature of said solvent.

11. The method according to claim 3, wherein the reductive methylating agent is a methylmetallic agent.

12. The method according to claim 11, wherein the methylmetallic agent is a methylmagnesium halide.

13. The method according to claim 12, wherein the methylmagnesium halide is methylmagnesium chloride.

14. The method according to claim 3, comprising reacting the compound of formula (VI) with the reductive methylating agent in the presence of an alkali metal halide.

15. The method of claim 4, comprising reacting the compound of formula (VIII) with the compound of formula (VII) in the presence of an organic base.

16. The method according to claim 15, wherein the organic base is a weak organic base.

17. The method according to claim 16, wherein the weak organic base is a tertiary amine.

18. The method according to claim 4, comprising reacting the compound of formula (VIII) with the compound of formula (VII) in the presence of a coupling agent.

19. The method of claim 2, wherein the aromatic hydrocarbon solvent is toluene.

20. The method of claim 14, wherein the alkali metal halide is lithium chloride.

21. The method of claim 17, wherein tertiary amine is N,N-diisopropylethylamine.

22. The method of claim 18, wherein the coupling agent is 2,4,6-tripropyl-1,3,5,2,4,6-trioxatriphosphinane 2,4,6-trioxide (T3P).

* * * * *